(12) United States Patent
Grzelak et al.

(10) Patent No.: US 7,414,058 B2
(45) Date of Patent: Aug. 19, 2008

(54) ADENOSINE $A_{2A}$ RECEPTOR ANTAGONISTS FOR THE TREATMENT OF EXTRA-PYRAMIDAL SYNDROME AND OTHER MOVEMENT DISORDERS

(75) Inventors: Michael Grzelak, Wayne, NJ (US); John Hunter, Warren, NJ (US); Annamarie Pond, Budd Lake, NJ (US); Geoffrey Varty, Cranford, NJ (US)

(73) Assignee: Schering Corporation, Kenilworth, NJ (US)

( * ) Notice: Subject to any disclaimer, the term of this patent is extended or adjusted under 35 U.S.C. 154(b) by 372 days.

(21) Appl. No.: 10/738,906

(22) Filed: Dec. 17, 2003

(65) Prior Publication Data

US 2004/0138235 A1    Jul. 15, 2004

Related U.S. Application Data

(60) Provisional application No. 60/435,321, filed on Dec. 19, 2002.

(51) Int. Cl.
*A61K 31/497* (2006.01)
*A61K 31/519* (2006.01)
*A01N 43/54* (2006.01)
*C07D 239/00* (2006.01)
*C07D 403/14* (2006.01)
*C07D 487/14* (2006.01)

(52) U.S. Cl. .................. 514/252.16; 544/251; 544/370; 544/371; 514/267

(58) Field of Classification Search ............ 514/252.16, 514/267
See application file for complete search history.

(56) References Cited

U.S. PATENT DOCUMENTS

| 5,565,460 | A | 10/1996 | Suzuki et al. |
| 5,935,964 | A | 8/1999 | Baraldi et al. |
| 6,630,475 | B2 | 10/2003 | Neustadt et al. |

FOREIGN PATENT DOCUMENTS

| WO | WO 95/01356 | | 1/1995 |
| WO | WO 99/26627 | | 6/1999 |
| WO | WO 00/13682 | | 3/2000 |
| WO | WO 01/02409 | A1 | 1/2001 |
| WO | WO01/92264 | * | 12/2001 |
| WO | WO 02/055083 | | 7/2002 |
| WO | WO 02/080957 | A1 | 10/2002 |
| WO | WO 03/032996 | A1 | 4/2003 |
| WO | WO 03/048163 | | 6/2003 |
| WO | WO 03/048163 | A1 | 6/2003 |
| WO | WO 03/048164 | A2 | 6/2003 |
| WO | WO 03/048165 | | 6/2003 |
| WO | WO 03/063876 | | 8/2003 |
| WO | WO2004/019949 | * | 3/2004 |
| WO | WO 2004/094431 | A2 | 11/2004 |

OTHER PUBLICATIONS

The Merck Manual of Diagnosis and Therapy, Seventeenth Edition, (1999) Beers et al., eds., Published by Merck Research Laboratories, p. 1416.*
Chemical Abstracts Registry No. 160098-96-4, entered into STN Jan. 12, 1995.*
Andrew L. Chesson et al., "Sleep", *J. of Sleep and Sleep Disorders Research*, 22(7):961-968 (1999).
Patti R. Weimerskirch et al., "Newer Dopamine Agonists in the Treatment of Restless Legs Syndrome", *The Annals of Pharmacotherapy*, 35(5):627-630, 2001.
M. Saletu et al., "Sleep Laboratory Studies in Restless Legs Syndrome Patients as Compared with Normals and Acute Effects of Ropinirole", *Neuropsychobiology*, 41(4):190-199, (2000).
Chartoff et al, *JPET*, 291 (1999), p. 531-537.
Ward et al, *Neuroscience*, 89, 3 (1999), p. 927-938.
Pinna et al, *Neuropsychopharmacology*, 20, 1 (1999), p. 44-51.
Wardas et al, *Synapse*, 41 (2001), p. 160-171.
Morelli et al, *Neurotoxicity Res.*, 3, (2001), p. 545-556.
Kanda et al, *Eur. J. Pharmacol.*, 256 (1994), p. 263-268.
Kuwana et al, *Abstracts of the Society for Neuroscience*, 23 (1997), p. 297 (abstract 119-14).
Shiozaki et al, *Psychopharmacology*, 147 (1999), p. 90-95.
Adami et al, *Brit. J. Pharmacol.*, 126, Proc. Supp. Mar. 1999, abstract 283P.
Ongini et al, *Drug. Development Research*, 52 (2001), p. 379-386.
Ongini et al, *Drug. Development Research*, 39 (1996), p. 450-460.
Correa et al, *Society for Neuroscience Abstract Viewer/Itinerary Planner*, (2002), abstract 885.8.
Parsons et al, J. Neurochemistry, 65 (1995), p. 2057-2064.
Mally et al, *Pharmacol. Ther.*, 72, 3 (1996), p. 243-250.
Ferre et al, *Curr. Med. Chem.—Central Nervous System Agents*, 3 (2003), p. 1-26.
Richter, Angelika et al., "Effects of adenosine receptor agonists and antagonists in a genetic animal model of primary paroxysmal dystonia", British Journal of Pharmacology, 134:343-352 (2001).
Del Carmen Parra Cid, M. et al., "A New Derivate of the Xanthine: A15Bu Improve The Motor Function", Society for Neuroscience 2002 Abstract Viewer and Itinerary Planner, Program No. 165. 15.

(Continued)

*Primary Examiner*—Shaojia Anna Jiang
*Assistant Examiner*—Eric S Olson
(74) *Attorney, Agent, or Firm*—Krishna G. Banerjee; William Y. Lee

(57) ABSTRACT

There is disclosed a method for the treatment of Extra Pyramidal syndrome (EPS) comprising the administration of an adenosine A2a receptor antagonist, alone or in combination with other agents useful for treating EPS.

8 Claims, 1 Drawing Sheet

OTHER PUBLICATIONS

De Sarro, G. et al., "Repeated treatment with adenosine A1 receptor agonist and antagonist modifies the anticonvulsant properties of CPPene", European Journal of Pharmacology 317:239-245 (1996).

Khan, G. M. et al., "Anticonvulsant effect and neurotransmitter modulation of focal and systemic 2-chloroadenosine against the development of pilocarpine-induced seizures", Neuropharmacology 39:2418-2432 (2000).

Seubert, C. N. et al., "Midazolam Selectively Potentiates the A2A—but not A1-receptor-mediated Effects of Adenosine", Anesthesiology, 92(2):567-577 (Feb. 2000).

Pond, A. et al., "Adenosine A2A Receptor Antagonists Attenuate Haloperidol-Induced Motor Impairments in Cebus Apella and Squirrel Monkeys", Department of Neurobiology, Schering-Plough Research Institute Poster.

Coffin, V. L. et al., "Acute Extrapyramidal Syndrome in Cebus Monkeys: Development Mediated by Dopamine D2 But Not D1 Receptors1", The Journal of Pharmacology and Experimental Therapeutics, 249(3):769-74 (1989).

Casey, D. E., "Behavioral effects of sertindole, risperidone, clozapine and haloperidol in Cebus monkeys", Psychopharmacology 124:134-140 (1996).

Povlsen, U. J. et al., "Effects of Serotonergic and Anticholinergic Drugs in Haloperidol-Induced Dystonia in Cebus Monkeys", Clinical Neuropharmacology 9(1):84-90 (1986).

Casey, D. E., "Serotonergic and dopaminergic aspects of neuroleptic-induced extrapyramidal syndromes in nonhuman primates", Psychopharmacology 112:S55-S59 (1993).

Casey, D. E., "Behavioral Effects of Long-Term Neuroleptic Treatment in Cebus Monkeys", Psychopharmacology Supplementum 2:211-216 (1985).

De Sarro, G. et al., "Effects of Adenosine receptor agonists and antagonists on audiogenic seizure-sensible DBAS/2 mice", European Journal of Pharmacology 371:137-145 (1999).

European Search Report for Application No. EP 03 81 8838 dated Sep. 25, 2006.

Bekar, Lane, et al; "Adenosine is crucial for deep brain stimulation—mediated attenuation of tremor", Nature Medicine, 14(1): 75-80 (2008).

Kochanek, Patrick M., et al; "Adenosine $A_1$ receptor knockout mice develop lethal status epilepticus after experimental traumatic brain injury", Journal of Cerebral Blood Flow & Metabolism, 26(4): (2006): Abstract of article only.

Reichelt, Melissa E., et al; "Genetic Deletion of the $A_1$ Adenosine Receptor Limits Myocardial Ischemic Tolerance", Circulation Research, 96: 363-367 (2005).

Hoffman, D.C., et al; "Catalepsy as a rodent model for detecting antipsychotic drugs with extrapyramidal side effect liability", Psychopharmacology, 120: 128-133 (1995).

* cited by examiner

ADENOSINE $A_{2A}$ RECEPTOR ANTAGONISTS FOR THE TREATMENT OF EXTRA-PYRAMIDAL SYNDROME AND OTHER MOVEMENT DISORDERS

CROSS REFERENCE TO RELATED APPLICATIONS

This application claims the benefit of U.S. Provisional Application 60/435,321, filed Dec. 19, 2002.

FIELD OF THE INVENTION

The present invention relates to the use of adenosine $A_{2a}$ receptor antagonists for the treatment of a variety of neurological syndromes involving the extra-pyramidal motor system (i.e. Extra-Pyramidal Syndrome) that occur following the acute and chronic use of almost all antipsychotic drugs. The invention also relates to the use of adenosine $A_{2a}$ receptor antagonists for the treatment of other abnormal movement disorders such as restless leg syndrome (RLS) and periodic limb movement in sleep (PLMS).

BACKGROUND OF THE INVENTION

Extra-Pyramidal Syndrome (EPS) is a collective term for a series of adverse neurological reactions associated with the use of antipsychotic drugs. There are six different categories of EPS-related neurological syndromes of which four, dystonia, akathisia, pseudoparkinsonism (parkinsonian syndrome), and tardive dyskinesia, are particularly prevalent in patients taking antipsychotic medication. Dystonia is a painful spasm of the muscle groups of, in particular, the neck, jaw, back, pharynx, and larynx. It is most common in young males being treated with antipsychotic drugs, but can also be associated with the use of cocaine, tricyclic antidepressants, lithium and anticonvulsants such as phenytoin and carbamazepine. Pseudoparkinsonism manifests itself as akinesia (rigidity, stiffness and slow voluntary motion, stooped, shuffling walk) and tremor and these symptoms develop within weeks or months after initiation of therapy. Akathisia manifests itself as strong, subjective inner feelings of distress or discomfort characterized by motor restlessness. Often mistaken for agitation or anxiety, this common syndrome is frequently under-diagnosed and is the least responsive to treatment. Tardive dyskinesia is a late-appearing syndrome associated with chronic use of neuroleptic drugs. It occurs more frequently in older patients and is characterized by stereotypical, repetitive, involuntary, quick choreiform movements of the face, eyelids, mouth, tongue, extremities and trunk.

EPS is more prevalent with the use of typical antipsychotic agents but has also been reported with the use of atypical agents. Typical antipsychotics include loxapine, haloperidol, chlorpromazine, prochlorperazine and thiothixene. Atypical antipsychotics include clozapine, olanzapine, loxapine, quetiapine, ziprasidone and risperidone.

Akathisia is also a characteristic of RLS and PLMS, as well as PLMD (periodic leg (or limb) movement disorder). RLS is a common disorder that causes patients to have an irresistible and unpleasant desire to move their legs; it usually manifests during periods of inactivity and/or at night, and can disturb sleep. Patients who do not have the typical RLS symptoms, but who do exhibit periodic leg movements that adversely impact sleep, are diagnosed with PLMS. Treatments for RLS and PLMS have included levodopa/carbidopa, levodopa/ benserazide, dopamine agonists such as pramipexole and ropinerole, benzodiazepines, opioids, anticonvulsants and iron (ferrous sulfate). RLS and PLMS have been extensively described in the literature, for example by Saletu et al, *Neuropsychobiology*, 41, 4 (2000), p. 190-9.

The purine nucleotide, adenosine, is known to be an endogenous modulator of a number of physiological functions in the central (CNS) and peripheral nervous systems.

Adenosine exerts its biological actions through a class of membrane specific receptors which belong to the super family of receptors coupled with G proteins. Biochemical and pharmacological studies, together with advances in molecular biology, have allowed the identification of at least four subtypes of adenosine receptors: $A_1$, $A_{2a}$, $A_{2b}$ and $A_3$. Analogs of adenosine able to interact as antagonists with the $A_1$, $A_{2a}$, $A_{2b}$ and $A_3$ receptors have also been identified.

In the CNS, data has shown that $A_{2a}$ receptors are present in high density in the basal ganglia, known to be important in the control of fine motor movement. Moreover, selective antagonists for the $A_{2a}$ receptor are of pharmacological interest because of their demonstrated efficacy in reducing motor impairment thereby improving function in neurodegenerative diseases such as Parkinson's disease and related movement disorders (e.g. Huntington's Disease). $A_{2a}$ antagonists appear to demonstrate a reduced side-effect liability (e.g. no dyskinesia) compared to current dopaminergic therapies resulting in an improved therapeutic index. $A_{2a}$ antagonists may also have antidepressant properties and stimulate cognitive functions. Some xanthine-related compounds have been found to be $A_1$ receptor selective antagonists, and xanthine and nonxanthine compounds have been found to have high $A_{2a}$ affinity with varying degrees of $A_{2a}$ vs. $A_1$ selectivity. Adenosine $A_{2a}$ receptor antagonists have been disclosed previously, for example in WO 95/01356 and U.S. Pat. No. 6,630,475.

SUMMARY OF THE INVENTION

This invention relates to a method for the treatment or prevention of Extra-Pyramidal Syndrome (e.g., dystonia, akathisia, pseudoparkinsonism and tardive dyskinesia) comprising administering a therapeutically effective amount of an adenosine $A_{2a}$ receptor antagonist to a patient in need thereof. In particular, this method is for the treatment or prevention of EPS in patients treated with an antipsychotic agent that has the side effect of inducing EPS. The adenosine $A_{2a}$ receptor antagonist can be administered after the symptoms of EPS have manifested, or an adenosine $A_{2a}$ receptor antagonist can be administered at the onset of administering an antipsychotic agent in order to prevent EPS from occurring. The invention, therefore, also includes a method of treating or preventing EPS induced by an antipsychotic agent comprising administering a combination of an antipsychotic agent and an adenosine $A_{2a}$ antagonist to a patient in need thereof. More particularly, the invention relates to the method of using of certain adenosine $A_{2a}$ antagonists for the monotherapy or the combined therapy.

The invention also relates to the treatment of primary (idiopathic) dystonia, and to the treatment or prevention of dystonia in patients who exhibit dystonia as a result of treatment with a tricyclic antidepressant, lithium or an anticonvulsant, or who have used cocaine, comprising administering a therapeutically effective amount of an adenosine $A_{2a}$ receptor antagonist to a patient in need thereof. When dystonia is caused by treatment with a tricyclic antidepressant, lithium or an anticonvulsant, the adenosine $A_{2a}$ receptor antagonist can be administered after the symptoms of dystonia have manifested, or an adenosine $A_{2a}$ receptor antagonist can be administered at the onset of administering a tricyclic antidepressant, lithium or an anticonvulsant in order to prevent dystonia from occurring. The invention, therefore, also includes a method of treating or preventing dystonia induced by a tricyclic antidepressant, lithium or an anticonvulsant comprising administering a combination of an adenosine $A_{2a}$ antagonist and a tricyclic antidepressant, lithium or an anticonvulsant to a patient in need thereof.

The invention also relates to the treatment of RLS or PLMS, comprising administering to a patient in need thereof a therapeutically effective amount of an adenosine $A_{2a}$ receptor antagonist. The invention also comprises a method of treating RLS or PLMS comprising administering a combination of an adenosine $A_{2a}$ antagonist with another agent useful in treating RLS or PLMS, such as levodopa/carbidopa, levodopa/benserazide, a dopamine agonist, a benzodiazepine, an opioid, an anticonvulsant or iron, to a patient in need thereof.

In another aspect, this invention relates to a kit comprising, in separate containers in a single package, pharmaceutical compositions for use in combination to treat or prevent EPS caused by treatment with antipsychotic agent, wherein one container comprises a pharmaceutical composition comprising an effective amount of an adenosine $A_{2a}$ receptor antagonist in a pharmaceutically acceptable carrier, and wherein a separate container comprises a pharmaceutical composition comprising an effective amount of an antipsychotic agent.

In another aspect, this invention relates to a kit comprising, in separate containers in a single package, pharmaceutical compositions for use in combination to treat or prevent dystonia caused by treatment with a tricyclic antidepressant, lithium or an anticonvulsant, wherein one container comprises a pharmaceutical composition comprising an effective amount of an adenosine $A_{2a}$ receptor antagonist in a pharmaceutically acceptable carrier, and wherein a separate container comprises a pharmaceutical composition comprising an effective amount of a tricyclic antidepressant, lithium or an anticonvulsant.

In another aspect, this invention relates to a kit comprising, in separate containers in a single package, pharmaceutical compositions for use in combination to treat RLS or PLMS, wherein one container comprises a pharmaceutical composition comprising an effective amount of an adenosine $A_{2a}$ receptor antagonist in a pharmaceutically acceptable carrier, and wherein a separate container comprises a pharmaceutical composition comprising an effective amount of levodopa/carbidopa, levodopa/benserazide, a dopamine agonist, a benzodiazepine, an opioid, an anticonvulsant or iron.

The invention also relates to the use of an adenosine $A_{2a}$ receptor antagonist for the preparation of a medicament for treating or preventing EPS, dystonia, RLS or PLMS, alone or in combination with the other agents discussed above.

DETAILED DESCRIPTION OF THE DRAWINGS

A more complete understanding of the invention may be obtained by reading the following description in conjunction with the appended figures relating to haloperidol-induced EPS in *Cebus apella* monkeys.

DETAILED DESCRIPTION OF THE INVENTION

Figure 1A:
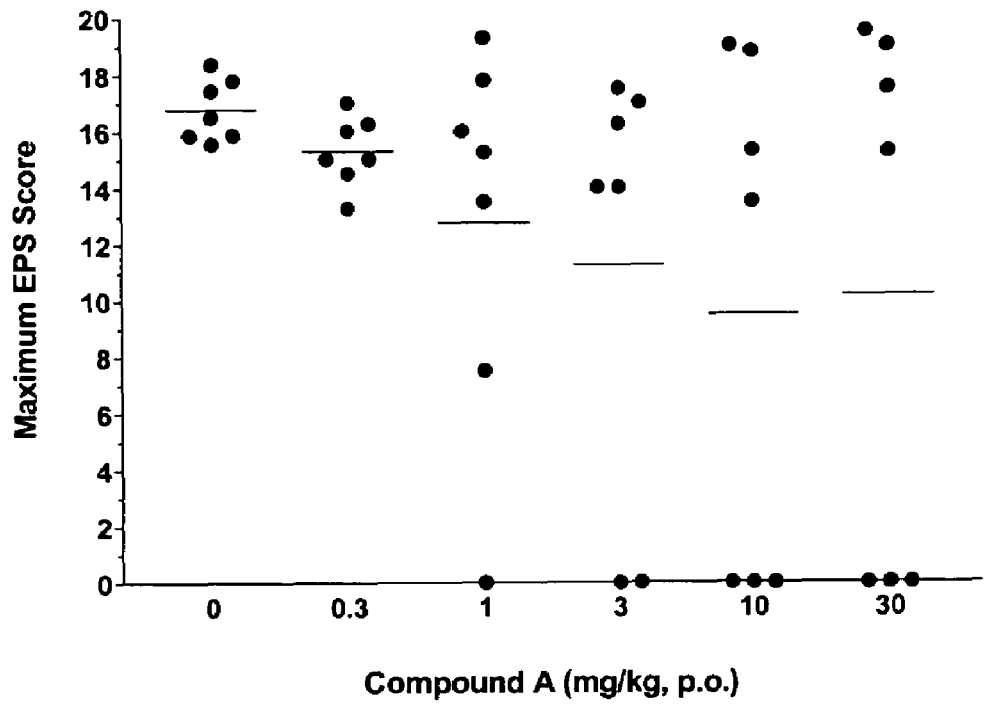
FIG. 1A illustrates the effect of Compound A (1-30 mg/kg, p.o.) on maximum EPS score.

Any adenosine $A_{2a}$ receptor antagonist is contemplated for use in the method of this invention. Suitable adenosine $A_{2a}$ receptor antagonists useful in the method of the invention can be identified by the binding assay described below. Specific examples of suitable adenosine $A_{2a}$ antagonists include the compounds disclosed in several patents and patent applications, e.g. WO 95/01356; U.S. Pat. Nos. 5,565,460; 6,630,475 B2; 5,935,964; WO 03/032996; WO 03/048165; WO 03/048164; WO 03/048163; and WO 01/02409. Specifically, these patents and applications disclose the following compounds.

U.S. Pat. No. 6,630,475 B2 discloses compounds having the structural formula I

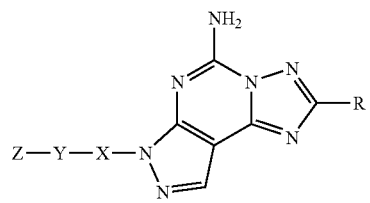

or a pharmaceutically acceptable salt thereof, wherein
R is $R^1$-furanyl, $R^1$-thienyl, $R^1$-pyridyl, $R^1$-pyridyl N-oxide, $R^1$-oxazolyl, $R^{10}$-phenyl, $R^1$-pyrrolyl or $C_4$-$C_6$ cycloalkenyl;
X is $C_2$-$C_6$ alkylene or —C(O)$CH_2$—;
Y is —N($R^2$)$CH_2CH_2$N($R^3$)—, —O$CH_2CH_2$N($R^2$)—, —O—, —S—, —$CH_2$S—, —($CH_2$)$_2$—NH—, or

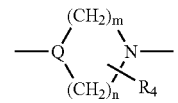

and
Z is $R^5$-phenyl, $R^5$-phenyl($C_1$-$C_6$)alkyl, $R^5$-heteroaryl, diphenylmethyl, $R^6$—C(O)—, $R^6$—$SO_2$—, $R^6$—OC(O)—, $R^7$—N($R^8$)—C(O)—, $R^7$—N($R^8$)—C(S)—,

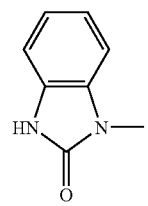

phenyl-CH(OH)—, or phenyl-C(=N$OR^2$)—; or when Q is

Z is also phenylamino or pyridylamino; or
Z and Y together are

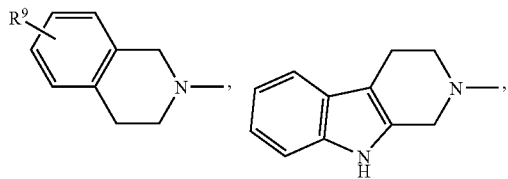

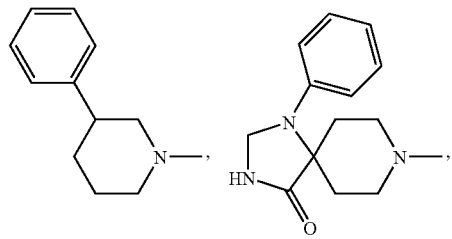

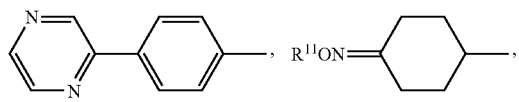

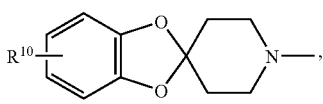

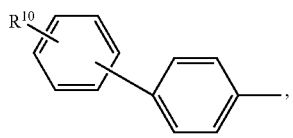

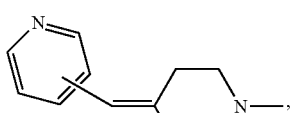

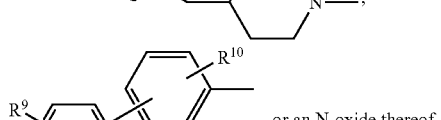

or an N-oxide thereof,

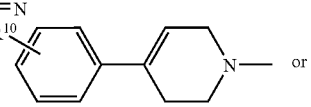

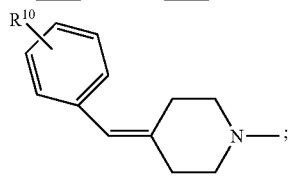

$R^1$ is 1 to 3 substituents independently selected from hydrogen, $C_1$-$C_6$-alkyl, —$CF_3$, halogen, —$NO_2$, —$NR^{12}R^{13}$, $C_1$-$C_6$ alkoxy, $C_1$-$C_6$ alkylthio, $C_1$-$C_6$ alkylsulfinyl, and $C_1$-$C_6$ alkylsulfonyl;

$R^2$ and $R^3$ are independently selected from the group consisting of hydrogen and $C_1$-$C_6$ alkyl;

m and n are independently 2-3;

Q is

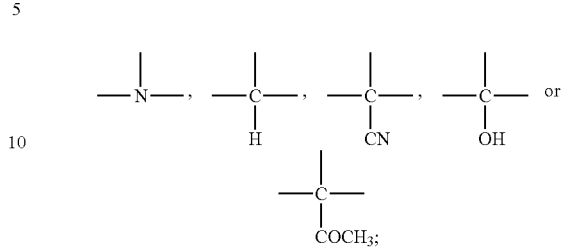

$R^4$ is 1-2 substituents independently selected from the group consisting of hydrogen and $C_1$-$C_6$alkyl, or two $R^4$ substituents on the same carbon can form =O;

$R^5$ is 1 to 5 substituents independently selected from the group consisting of hydrogen, halogen, $C_1$-$C_6$ alkyl, hydroxy, $C_1$-$C_6$ alkoxy, —CN, di-(($C_1$-$C_6$)alkyl)amino, —$CF_3$, —$OCF_3$, acetyl, —$NO_2$, hydroxy($C_1$-$C_6$)alkoxy, ($C_1$-$C_6$)-alkoxy($C_1$-$C_6$)alkoxy, di-(($C_1$-$C_6$)-alkoxy)($C_1$-$C_6$)alkoxy, ($C_1$-$C_6$)-alkoxy($C_1$-$C_6$)alkoxy-($C_1$-$C_6$)-alkoxy, carboxy($C_1$-$C_6$)-alkoxy, ($C_1$-$C_6$)-alkoxycarbonyl($C_1$-$C_6$)alkoxy, ($C_3$-$C_6$) cycloalkyl($C_1$-$C_6$)alkoxy, di-(($C_1$-$C_6$)alkyl)amino($C_1$-$C_6$) alkoxy, morpholinyl, ($C_1$-$C_6$)alkyl-$SO_2$—, ($C_1$-$C_6$)alkyl-SO—($C_1$-$C_6$)alkoxy, tetrahydropyranyloxy, ($C_1$-$C_6$) alkylcarbonyl($C_1$-$C_6$)-alkoxy, ($C_1$-$C_6$)-alkoxycarbonyl, ($C_1$-$C_6$)alkylcarbonyloxy($C_1$-$C_6$)-alkoxy, —$SO_2NH_2$, phenoxy,

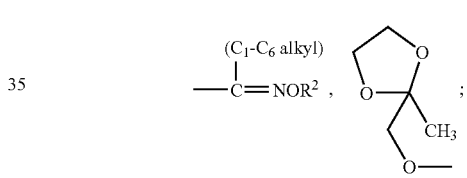

or adjacent $R^5$ substituents together are —O—$CH_2$—O—, —O—$CH_2CH_2$—O—, —O—$CF_2$—O— or —O—$CF_2CF_2$—O— and form a ring with the carbon atoms to which they are attached;

$R^6$ is ($C_1$-$C_6$)alkyl, $R^5$-phenyl, $R^5$-phenyl($C_1$-$C_6$)alkyl, thienyl, pyridyl, ($C_3$-$C_6$)-cycloalkyl, ($C_1$-$C_6$)alkyl-OC(O)—NH—($C_1$-$C_6$)alkyl-, di-(($C_1$-$C_6$)alkyl)aminomethyl, or

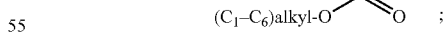

$R^7$ is ($C_1$-$C_6$)alkyl, $R^5$-phenyl or $R^5$-phenyl($C_1$-$C_6$)alkyl;

$R^8$ is hydrogen or $C_1$-$C_6$ alkyl; or $R^7$ and $R^8$ together are —$(CH_2)_p$—A—$(CH_2)_q$, wherein p and q are independently 2 or 3 and A is a bond, —$CH_2$—, —S— or —O—, and form a ring with the nitrogen to which they are attached;

$R^9$ is 1-2 groups independently selected from hydrogen, $C_1$-$C_6$ alkyl, hydroxy, $C_1$-$C_6$ alkoxy, halogen, —$CF_3$ and ($C_1$-$C_6$)alkoxy($C_1$-$C_6$)alkyl;

$R^{10}$ is 1 to 5 substituents independently selected from the group consisting of hydrogen, halogen, $C_1$-$C_6$ alkyl, hydroxy, $C_1$-$C_6$ alkoxy, —CN, —$NH_2$, $C_1$-$C_6$alkylamino, di-(($C_1$-$C_6$)alkyl)amino, —$CF_3$, —$OCF_3$ and —$S(O)_{0-2}$($C_1$-$C_6$)alkyl;

$R^{11}$ is H, $C_1$-$C_6$ alkyl, phenyl, benzyl, $C_2$-$C_6$ alkenyl, $C_1$-$C_6$ alkoxy($C_1$-$C_6$)alkyl, di-(($C_1$-$C_6$)alkyl)amino($C_1$-$C_6$)alkyl, pyrrolidinyl($C_1$-$C_6$)alkyl or piperidino($C_1$-$C_6$)alkyl;

$R^{12}$ is H or $C_1$-$C_6$ alkyl; and $R^{13}$ is ($C_1$-$C_6$)alkyl-C(O)— or ($C_1$-$C_6$)alkyl-$SO_2$—.

Preferred compounds of formula I are those wherein R is $R^1$-furanyl, $R^1$-thienyl, $R^1$-pyrrolyl or $R^{10}$-phenyl, more preferably $R^1$-furanyl. $R^1$ is preferably hydrogen or halogen. Another group of preferred compounds is that wherein X is alkylene, preferably ethylene. Y is preferably

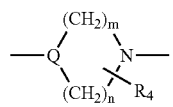

wherein Q is

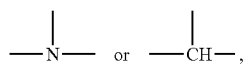

with Q preferably being nitrogen. Preferably, m and n are each 2, and $R^4$ is H. A preferred definition for Z is $R^5$-phenyl, $R^5$-heteroaryl, $R^6$—C(O)— or $R^6$—$SO_2$—. $R^5$ is preferably H, halogen, alkyl, alkoxy, hydroxyalkoxy or alkoxyalkoxy. $R^6$ is preferably $R^5$-phenyl.

Preferred specific compounds of formula I are those of the formula IA

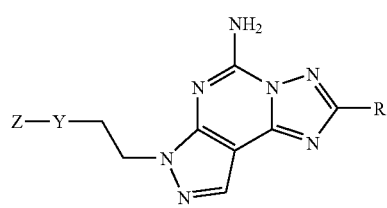

wherein R and Z—Y are as defined in the following table:

Other useful adenosine $A_{2a}$ receptor antagonists include those disclosed in WO 95/01356 as compounds having the structural formula II

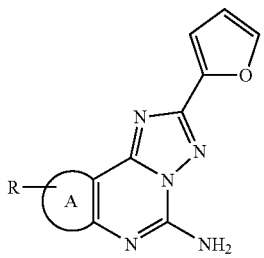

wherein:
A is pyrazole, imidazole or a triazole ring;
R is hydrogen; $C_1$-$C_8$ alkyl; $C_3$-$C_7$ alkenyl; $C_3$-$C_7$ alkynyl; $C_3$-$C_7$ cycloalkyl; $C_1$-$C_5$ alkyl substituted with one or more halogen atoms, hydroxy groups, $C_1$-$C_4$ alkoxy, $C_3$-$C_7$ cycloalkyl, groups of formula —$NR_1R_2$, —$CONR_1R_2$; aryl optionally substituted with halogen atoms, $C_1$-$C_4$ alkoxy groups, $C_1$-$C_4$ alkyl, nitro, amino, cyano, $C_1$-$C_4$ haloalkyl, $C_1$-$C_4$ haloalkoxy, carboxy, carboxyamido; $C_7$-$C_{10}$ aralkyl in which the aryl moiety can be substituted with one or more of the substituents indicated above for the aryl group; a group of formula —$(CH_2)_m$-Het, wherein Het is a 5-6 membered aromatic or non aromatic heterocyclic ring containing one or more heteroatoms selected from N, O, S and m is an integer from 1 to 5;
$R_1$, $R_2$ which are the same or different, are hydrogen, $C_1$-$C_5$ alkyl, $C_7$-$C_{10}$ aralkyl, phenyl, or taken together with the nitrogen they are linked to, form an azetidine ring or a 5-6 membered heterocyclic ring containing one or more heteroatoms such as N, O, S and n is an integer from 2 to 5.

Preferably, compounds of formula II are those wherein R is hydrogen, $C_1$-$C_8$ alkyl, aryl or $C_7$-$C_{10}$ aralkyl optionally substituted, preferably with halogen atoms.

U.S. Pat. No. 5,935,964 discloses useful adenosine $A_{2a}$ receptor antagonist compounds having the structural formula III

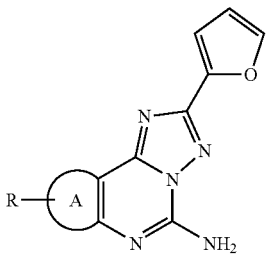

wherein A is pyrazole, imidazole or triazole ring;
R is

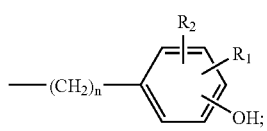

$R_1$ and $R_2$, which are the same or different, are H, OH, halogen, $C_1$-$C_4$ alkoxy, $C_1$-$C_4$ alkyl, nitro, amino, cyano, $C_1$-$C_4$ haloalkyl, $C_1$-$C_4$ haloalkoxy, carboxy or carboxamido; or the OH group, together with one of $R_1$ or $R_2$, or $R_1$ and $R_2$, can form a methylenedioxy group —O—$CH_2$—O—; and
n is an integer from 0-4.

Preferred compounds of formula III are those wherein A is pyrazolo[4,3-e] or 1,2,3-triazolo[5,4-e].

U.S. Pat. No. 5,565,460 discloses useful adenosine $A_{2a}$ receptor antagonist compounds having the structural formulas IVA and IVB, wherein formula IVA is

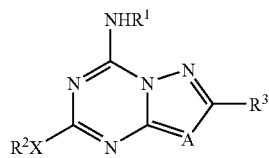

wherein $R^1$ represents hydrogen, substituted or unsubstituted lower alkyl, or substituted or unsubstituted lower alkanoyl;
$R^2$ represents hydrogen, substituted or unsubstituted lower alkyl, substituted or unsubstituted lower alkenyl, substituted or unsubstituted cycloalkyl, substituted or unsubstituted aryl, substituted or unsubstituted aralkyl, or a substituted or unsubstituted heterocyclic group;
$R^3$ represents a substituted or unsubstituted heterocyclic group;
X represents a single bond, O, S, S(O), S(O)$_2$, or $NR^4$ (in which $R^4$ represents hydrogen, or substituted or unsubstituted lower alkyl; or $R^2$ and $NR^4$ are combined to form a substituted or unsubstituted 4 to 6-membered saturated heterocyclic group): and
A represents N or $CR^5$ (in which $R^5$ represents hydrogen, or a substituted or unsubstituted lower alkyl); and wherein formula IVB is

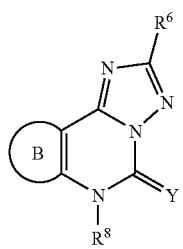

wherein $R^6$ represents substituted or unsubstituted aryl, or a substituted or unsubstituted heterocyclic group;
Y represents O, S, or $NR^7$ (in which $R^7$ represents substituted or unsubstituted lower alkyl, substituted or unsubstituted cycloalkyl, or substituted or unsubstituted aryl);
$R^8$ represents hydrogen, substituted or unsubstituted lower alkyl, substituted or unsubstituted lower alkenyl, substituted or unsubstituted lower alkynyl, substituted or unsubstituted cycloalkyl, substituted or unsubstituted aryl, substituted or unsubstituted aralkyl, or a substituted or unsubstituted heterocyclic group; and
B and the adjacent two carbon atoms are combined to form a substituted or unsubstituted, partially saturated or unsaturated, monocyclic or bicyclic, carbocyclic or heterocyclic group.

WO 03/032996 discloses useful adenosine $A_{2a}$ receptor antagonist compounds having the structural formula V

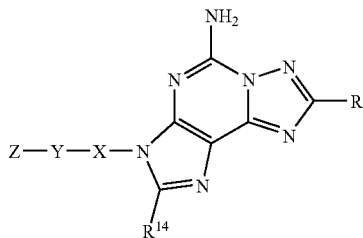

or a pharmaceutically acceptable salt thereof, wherein
R is $R^1$-heteroaryl, $R^{10}$-phenyl, $C_4$-$C_6$ cycloalkenyl, —C(=CH$_2$)CH$_3$, —C≡C—CH$_3$, —C≡C—CH$_2$—OR$^2$, —CH=C(CH$_3$)$_2$,

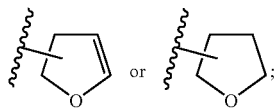

X is $C_1$-$C_6$ alkylene, —C(O)CH$_2$— or —C(O)N(R$^2$)CH$_2$—;
Y is —N(R$^2$)CH$_2$CH$_2$N(R$^3$)—, —OCH$_2$CH$_2$N(R$^2$)—, —O—, —S—, —CH$_2$S—, —(CH$_2$)$_{2-3}$—N(R$^2$)—, $R^5$-divalent heteroaryl,

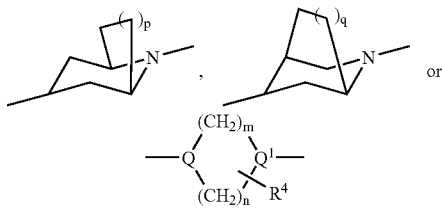

and
Z is $R^5$-phenyl, $R^5$-phenyl($C_1$-$C_6$)alkyl, $R^5$-heteroaryl, $R^5$-bicyclic heteroaryl, $R^5$-benzofused heteroaryl, diphenylmethyl or $R^6$—C(O)—;
or when Y is

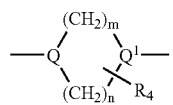

Z is also $R^6$—SO$_2$—, $R^7$—N(R$^8$)—C(O)—, $R^7$—N(R$^8$)—C(S)— or $R^6$OC(O)—;
or when Q is

Z is also phenylamino or pyridylamino;
or Z and Y together are

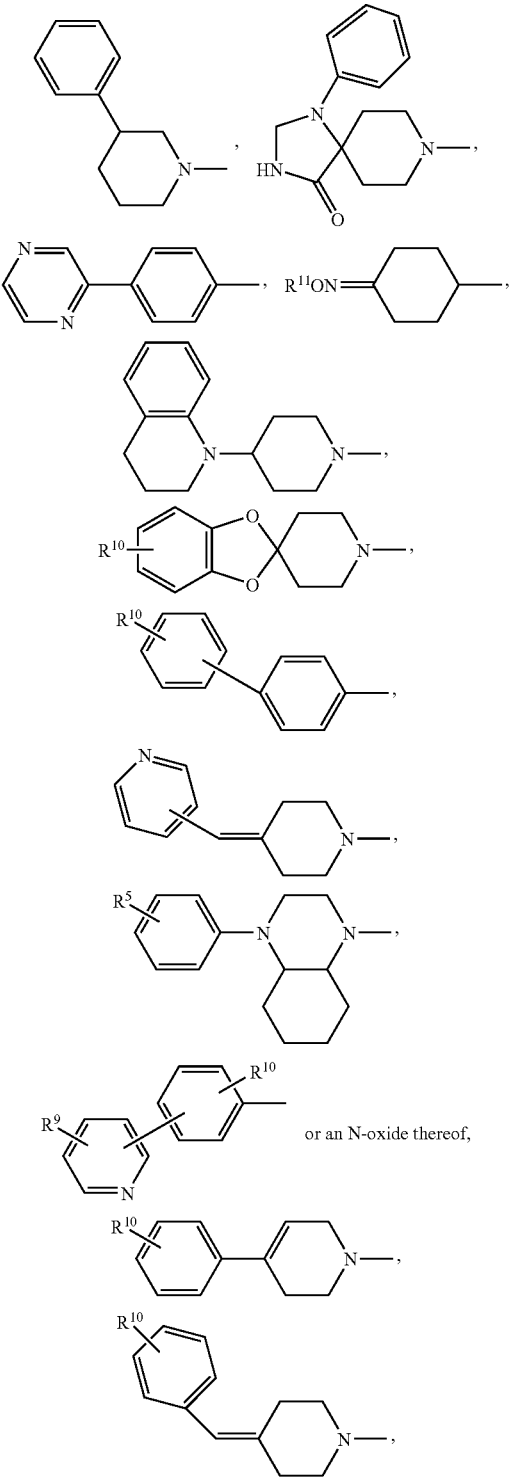

or an N-oxide thereof, or Y and Z together form a piperidinyl or pyrrolidinyl ring fused to a monocyclic or bicyclic aryl or a monocyclic or bicyclic heteroaryl ring wherein X is attached to the N atom of the piperidinyl or pyrrolidinyl ring;

$R^1$ is 1 to 3 substituents independently selected from hydrogen, $C_1$-$C_6$-alkyl, —$CF_3$, halogen, —$NO_2$, —$NR^{12}R^{13}$, $C_1$-$C_6$ alkoxy, $C_1$-$C_6$ alkylthio, $C_1$-$C_6$ alkylsulfinyl, $C_1$-$C_6$ alkylsulfonyl, —$COOR^7$ or —$C(O)NR^2R^3$;

$R^2$ and $R^3$ are independently selected from the group consisting of hydrogen and $C_1$-$C_6$ alkyl;

m and n are independently 2-3;

p and q are independently 0-2;

Q and $Q^1$ are independently selected from the group consisting of

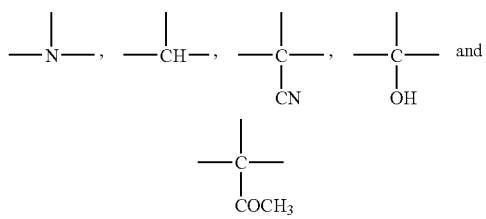

provided that at least one of Q and $Q^1$ is

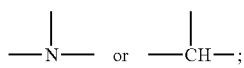

$R^4$ is 1-2 substituents independently selected from the group consisting of hydrogen, $C_1$-$C_6$alkyl, $R^1$-aryl and $R^1$-heteroaryl, or two $R^4$ substituents on the same carbon can form =O;

$R^5$ is 1 to 5 substituents independently selected from the group consisting of hydrogen, halogen, $C_1$-$C_6$ alkyl, hydroxy, $C_1$-$C_6$ alkoxy, —CN, di-(($C_1$-$C_6$)alkyl)amino, —$CF_3$, —$OCF_3$, acetyl, —$NO_2$, hydroxy($C_1$-$C_6$)alkoxy, ($C_1$-$C_6$)-alkoxy($C_1$-$C_6$)alkoxy, di-(($C_1$-$C_6$)-alkoxy)($C_1$-$C_6$)alkoxy, ($C_1$-$C_6$)-alkoxy($C_1$-$C_6$)alkoxy-($C_1$-$C_6$)-alkoxy, carboxy($C_1$-$C_6$)—alkoxy, ($C_1$-$C_6$)-alkoxycarbonyl($C_1$-$C_6$)alkoxy, ($C_3$-$C_6$)cycloalkyl($C_1$-$C_6$)alkoxy, di-(($C_1$-$C_6$)alkyl)amino($C_1$-$C_6$)alkoxy, morpholinyl, ($C_1$-$C_6$)alkyl-$SO_2$—, ($C_1$-$C_6$)alkyl-$SO_2$—($C_1$-$C_6$)alkoxy, tetrahydropyranyloxy, ($C_1$-$C_6$)alkylcarbonyl($C_1$-$C_6$)-alkoxy, ($C_1$-$C_6$)-alkoxycarbonyl, ($C_1$-$C_6$)alkylcarbonyloxy($C_1$-$C_6$)-alkoxy, —$SO_2NH_2$, phenoxy,

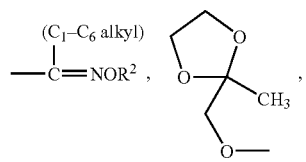

($R^2O)_2$—P(O)—$CH_2$—O— and ($R^2O)_2$—P(O)—; or adjacent $R^5$ substituents together are —O—$CH_2$—O—, —O—$CH_2CH_2$—O—, —O—$CF_2$—O— or —O—$CF_2CF_2$—O—and form a ring with the carbon atoms to which they are attached;

$R^6$ is ($C_1$-$C_6$)alkyl, $R^5$-phenyl, $R^5$-phenyl($C_1$-$C_6$)alkyl, thienyl, pyridyl, ($C_3$-$C_6$)-cycloalkyl, ($C_1$-$C_6$)alkyl-OC(O)—NH—($C_1$-$C_6$)alkyl-, di-(($C_1$-$C_6$)alkyl)aminomethyl, or

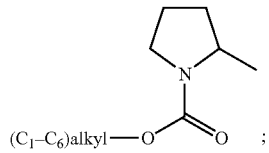

$R^7$ is ($C_1$-$C_6$)alkyl, $R^5$-phenyl or $R^5$-phenyl($C_1$-$C_6$)alkyl;

$R^8$ is hydrogen or $C_1$-$C_6$ alkyl; or $R^7$ and $R^8$ together are —($CH_2$)$_p$—A—($CH_2$)$_q$, wherein p and q are independently 2 or 3 and A is a bond, —$CH_2$—, —S— or —O—, and form a ring with the nitrogen to which they are attached;

$R^9$ is 1-2 substituents independently selected from the group consisting of hydrogen, $C_1$-$C_6$ alkyl, hydroxy, $C_1$-$C_6$ alkoxy, halogen, —$CF_3$ and ($C_1$-$C_6$)alkoxy-($C_1$-$C_6$)alkoxy;

$R^{10}$ is 1 to 5 substituents independently selected from the group consisting of hydrogen, halogen, $C_1$-$C_6$ alkyl, hydroxy, $C_1$-$C_6$ alkoxy, —CN, —$NH_2$, $C_1$-$C_6$alkylamino, di-(($C_1$-$C_6$)alkyl)amino, —$CF_3$, —$OCF_3$, —S(O)$_{0-2}$($C_1$-$C_6$)alkyl and —$CH_2$—$SO_2$-phenyl;

$R^{11}$ is H, $C_1$-$C_6$ alkyl, phenyl, benzyl, $C_2$-$C_6$ alkenyl, $C_1$-$C_6$ alkoxy($C_1$-$C_6$)alkyl, di-(($C_1$-$C_6$)alkyl)amino($C_1$-$C_6$)alkyl, pyrrolidinyl($C_1$-$C_6$)alkyl or piperidino($C_1$-$C_6$)alkyl;

$R^{12}$ is H or $C_1$-$C_6$ alkyl;

$R^{13}$ is H, ($C_1$-$C_6$)alkyl-C(O)— or ($C_1$-$C_6$)alkyl-$SO_2$—;

$R^{14}$ is H, halogen, $C_1$-$C_6$ alkyl, hydroxy($C_1$-$C_6$)alkyl, $C_1$-$C_6$ alkoxy($C_1$-$C_6$)alkyl, thio($C_1$-$C_6$)alkyl, ($C_1$-$C_6$)alkylthio($C_1$-$C_6$)alkyl or $NR^2R^3$—($C_1$-$C_6$)alkyl; and $R^{15}$ is H, halogen, $C_1$-$C_6$ alkyl or $C_1$-$C_6$ alkoxy.

Preferred compounds of formula V are those wherein R is $R^1$-furanyl, $R^1$-thienyl, $R^1$-pyrrolyl, $R^1$-pyridyl or $R^{10}$-phenyl, more preferably $R^1$-furanyl or $R^{10}$-phenyl. $R^1$ is preferably hydrogen or halogen. $R^{10}$ is preferably hydrogen, halogen, alkyl or —$CF_3$. Another group of preferred compounds is that wherein X is alkylene, preferably ethylene. Y is preferably

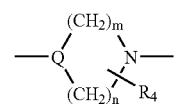

wherein Q is

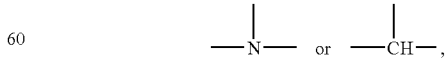

with Q preferably being nitrogen. Preferably, m and n are each 2, and $R^4$ is H. A preferred definition for Z is $R^5$-phenyl or $R^5$-heteroaryl. $R^5$ is preferably H, halogen, alkyl, alkoxy, hydroxyalkoxy or alkoxyalkoxy. $R^6$ is preferably $R^5$-phenyl.

Preferred specific compounds of formula V are those of the formula VA

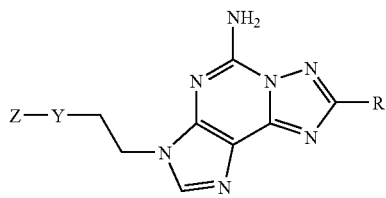

wherein R and Z—Y are as defined in the following table:

| Z—Y— | R |
|---|---|
| 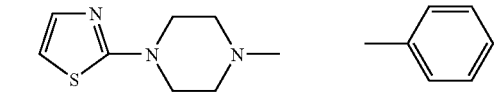 | 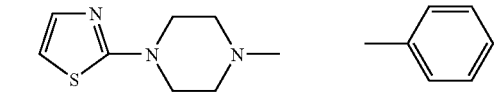 |
| 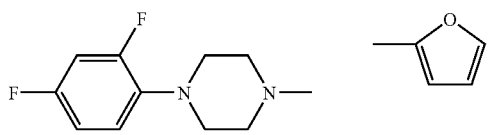 | 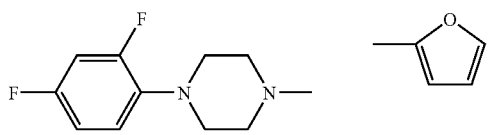 |
| 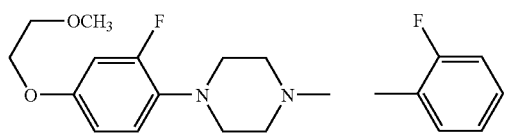 | 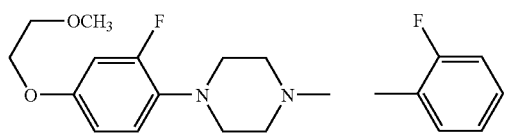 |
| 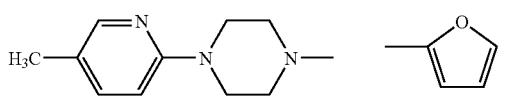 | 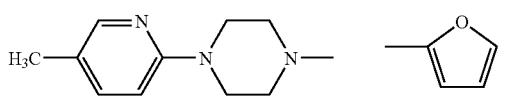 |
| 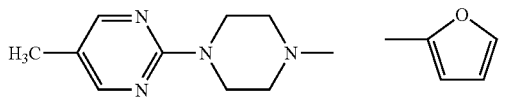 | 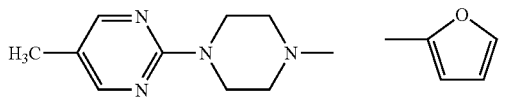 |
| 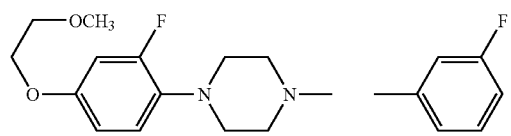 | 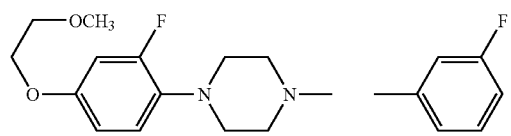 |

-continued

| Z—Y— | R |
|---|---|
| 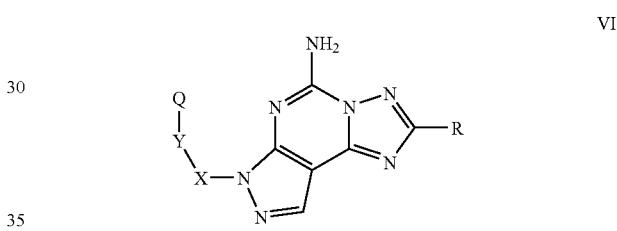 | 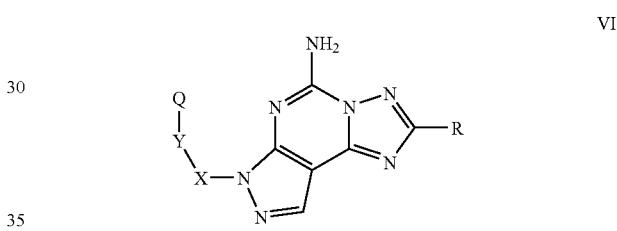 |

WO 03/048165 discloses useful adenosine $A_{2a}$ receptor antagonist compounds having the structural formula VI

VI or a pharmaceutically acceptable salt or solvate of said compound, wherein:

R is selected from the group consisting of $R^1$-furanyl-, $R^1$-thienyl-, $R^1$-pyridyl-, $R^1$-oxazolyl-, $R^1$-pyrrolyl- and $R^2$-aryl-;

X is —$(CH_2)_n$—;

Y is a piperidinyl, pyrrolidinyl or azepanyl group with an aryl or heteroaryl moiety fused to two adjacent carbon atoms on Y, wherein X is attached to the N atom of the piperidinyl, pyrrolidinyl or azepanyl group;

Q is 1-4 substituents, which can be the same or different, and are independently selected from the group consisting of hydrogen, cycloalkyl, cycloheteroalkyl, amino, aryl, aralkyl, heteroaryl, alkyl, $CF_3$, CN, halogen, $NO_2$, alkoxy, alkoxyalkoxy, cycloalkylalkoxy, acyloxy, alkylamino, acylamino, alkylsulfonamino, alkylaminosulfonyl, dialkylaminosulfonyl, $NH_2SO_2$—, and hydroxy;

n is 1 to 4;

$R^1$ is 1-3 substituents, which may be the same or different, and are independently selected from the group consisting of hydrogen, alkyl, $CF_3$, halogen and $NO_2$; and $R^2$ is 1-3 substituents, which may be the same or different, and are independently selected from the group consisting of hydrogen, alkyl, $CF_3$, halogen, $NO_2$, alkoxy, acyloxy, alkylamino, acylamino, alkylsulfonamido, alkylaminosulfonyl, dialkylaminosulfonyl, aminosulfonyl, and hydroxyl.

In a preferred embodiment of compounds of formula VI, Y is

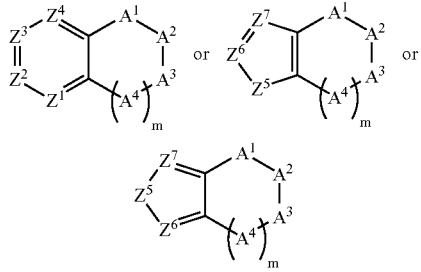

wherein $A^1$ is N—X, and $A^2$ and $A^3$ each are $CR^4R^5$, or
$A^1$ and $A^3$ each are $CR^4R^5$, and $A^2$ is N—X, or
$A^1$ and $A^2$ each are $CR^4R^5$, and $A^3$ is N—X;
$A^4$ is $CR^4R^5$;
$Z^1$, $Z^2$, $Z^3$ and $Z^4$, which can the same or different, are each independently selected from the group consisting of N and $CR^3$, provided that 0-2 of $Z^1$, $Z^2$, $Z^3$ or $Z^4$ are N and the remainder are $CR^3$;
$Z^5$ is $NR^5$, O, S or $CR^4R^5$;
$Z^6$ is N or $CR^3$;
$Z^7$ is N or $CR^3$;
m is an integer from 0 to 2;
$R^3$ is selected from the group consisting of hydrogen, cycloalkyl, amino, aryl, heteroaryl, $C_1$-$C_6$-alkyl, $CF_3$, CN, halogen, $NO_2$, $C_1$-$C_6$-alkoxy, $C_1$-$C_6$-acyloxy, $C_1$-$C_6$-alkylamino, $C_1$-$C_6$-acylamino, $C_1$-$C_6$-alkylsulfonamino, $C_1$-$C_6$-alkylaminosulfonyl, $C_1$-$C_6$-dialkylaminosulfonyl, $NH_2$—$SO_2$—, and hydroxy;
$R^4$ is selected from the group consisting of hydrogen, hydroxyalkyl, aryl, aralkyl, $C_1$-$C_6$-alkyl, $C_1$-$C_6$-alkoxy, $CF_3$, CN, halogen, hydroxy, and $NO_2$; and
$R^5$ is hydrogen or $C_1$-$C_6$ alkyl.

Preferred specific examples of compounds of formula VI include compounds of the formula:

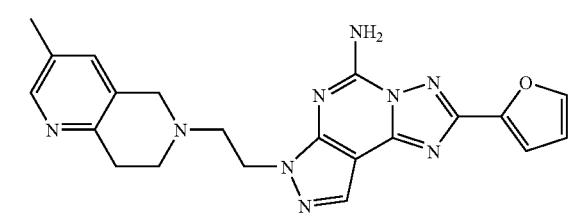

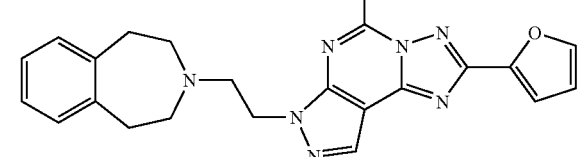

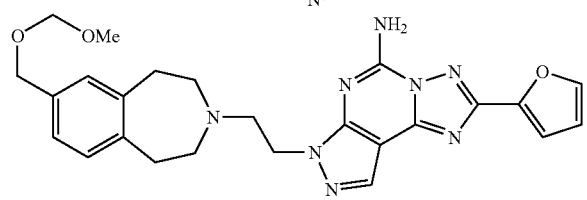

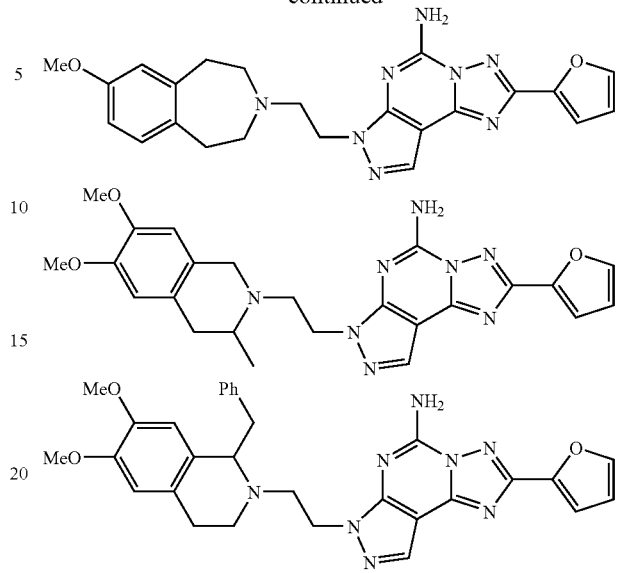

WO 03/048164 discloses useful adenosine $A_{2a}$ receptor antagonist compounds having the structural formula VII

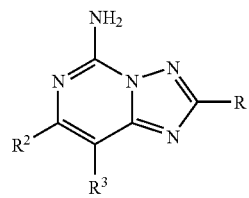

or a pharmaceutically acceptable salt or solvate thereof; wherein:
R is selected from the group consisting of $R^4$-heteroaryl, $R^5$-phenyl, $(C_4$-$C_6)$cycloalkenyl, —C(=$CH_2$)$CH_3$, —C≡C—$CH_3$,

—CH=C($CH_3$)$_2$,

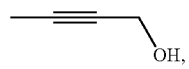

and —CH=CH—$CH_3$;
$R^2$ is selected from the group consisting of —W—X, —$NR^{19}$($CH_2$)$_m$—W—X, and —$NR^{19}$CH($CH_3$)—W—X, or
$R^2$ is selected from the group consisting of alkyl, alkenyl and —$NR^{18}R^{19}$, wherein said alkyl, alkenyl or —$NR^{18}R^{19}$ is optionally substituted by —W—X;
$R^3$ is selected from the group consisting of H, halo, alkyl, trifluoromethyl, alkoxy, alkoxyalkyl, hydroxyalkyl, alkylamino, alkylaminoalkyl, dialkylamino, dialkylaminoalkyl, aminoalkyl, aryl, heteroaryl, and CN;

$R^4$ is 1 to 3 substituents, which can be the same or different, and are independently selected from the group consisting of hydrogen, $(C_1-C_6)$-alkyl, —$CF_3$, halogen, —$NO_2$, —$NR^{15}R^{16}$, $(C_1-C_6)$alkoxy, $(C_1-C_6)$alkylthio, $(C_1-C_6)$alkylsulfinyl, $(C_1-C_6)$alkylsulfonyl, —$COOR^{17}$ and —$C(O)NR^6R^7$;

$R^5$ is 1 to 5 substituents, which can be the same or different, and are independently selected from the group consisting of hydrogen, halogen, $(C_1-C_6)$alkyl, hydroxy, $(C_1-C_6)$alkoxy, —CN, —$NH_2$, $(C_1-C_6)$alkylamino, di-$((C_1-C_6)$alkyl)amino, —$CF_3$, —$OCF_3$, —$S(O)_{0-2}(C_1-C_6)$alkyl and —$CH_2$—$SO_2$-phenyl;

$R^6$ and $R^7$, which can be the same or different, are each independently selected from the group consisting of hydrogen and $(C_1-C_6)$alkyl;

$R^8$ is 1 to 5 substituents, which can be the same or different, and are independently selected from the group consisting of hydrogen, halogen, $(C_1-C_6)$alkyl, hydroxy, $C_1-C_6$ alkoxy, —CN, amino, di-$((C_1-C_6)$alkyl)amino, —$CF_3$, —$OCF_3$, acetyl, —$NO_2$, hydroxy$(C_1-C_6)$alkoxy, $(C_1-C_6)$-alkoxy$(C_1-C_6)$alkoxy, di-$((C_1-C_6)$-alkoxy)$(C_1-C_6)$alkoxy, $(C_1-C_6)$-alkoxy$(C_1-C_6)$alkoxy-$(C_1-C_6)$-alkoxy, carboxy$(C_1-C_6)$-alkoxy, $(C_1-C_6)$-alkoxycarbonyl$(C_1-C_6)$alkoxy, $(C_3-C_6)$-cycloalkyl$(C_1-C_6)$alkoxy, di-$((C_1-C_6)$alkyl)amino$(C_1-C_6)$alkoxy, morpholinyl, $(C_1-C_6)$alkyl-$SO_2$—, $(C_1-C_6)$alkyl-$SO_2$—$(C_1-C_6)$alkoxy, tetrahydropyranyloxy, $(C_1-C_6)$alkylcarbonyl$(C_1-C_6)$-alkoxy, $(C_1-C_6)$-alkoxycarbonyl, $(C_1-C_6)$alkylcarbonyloxy$(C_1-C_6)$-alkoxy, —$SO_2NH_2$, phenoxy,

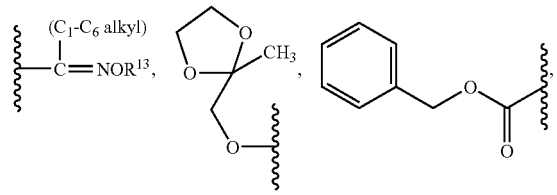

—O—$CH_2$—$P(O)(OR^6)_2$,— and —$P(O)(OR^6)_2$; or adjacent $R^8$ substituents together are —O—$CH_2$—O—, —O—$CH_2CH_2$—O—, —O—$CF_2$—O— or —O—$CF_2CF_2$—O— and form a ring with the carbon atoms to which they are attached;

$R^9$ is selected from the group consisting of $(C_1-C_6)$alkyl, $R^8$-aryl-, $R^8$-aryl$(C_1-C_6)$alkyl-, thienyl, pyridyl, $(C_3-C_6)$-cycloalkyl, $(C_1-C_6)$alkyl-OC(O)—NH—$(C_1-C_6)$alkyl-, di-$((C_1-C_6)$alkyl)aminomethyl, cycloheteroalkyl$(C_1-C_6)$alkyl, aryloxy$(C_1-C_6)$alkyl, alkoxy$(C_1-C_6)$alkyl and

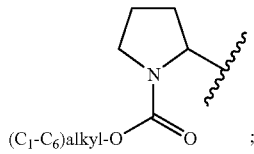

$R^{10}$ is 1-2 substituents, which can be the same or different, and are independently selected from the group consisting of hydrogen, $(C_1-C_6)$alkyl, $R^5$-aryl and $R^4$-heteroaryl, or two $R^{10}$ substituents on the same carbon can form =O;

$R^{11}$ is hydrogen or $(C_1-C_6)$alkyl; —C(O)alkyl, or $R^{17}$ and $R^{11}$ taken together are —$(CH_2)_p$—A—$(CH_2)_q$, wherein p and q are each independently 2 or 3 and A is selected from the group consisting of a bond, —$CH_2$—, —S— and —O—, and form a ring with the nitrogen to which they are attached;

$R^{12}$ is 1-2 substituents, which can be the same or different, and are independently selected from the group consisting of hydrogen, $(C_1-C_6)$alkyl, hydroxy, $(C_1-C_6)$alkoxy, halogen, and —$CF_3$;

$R^{13}$ is selected from the group consisting of H, $(C_1-C_6)$alkyl, phenyl, benzyl, $(C_2-C_6)$alkenyl, $(C_1-C_6)$alkoxy$(C_1-C_6)$alkyl, di-$((C_1-C_6)$alkyl)amino$(C_1-C_6)$alkyl, pyrrolidinyl$(C_1-C_6)$alkyl and piperidino$(C_1-C_6)$alkyl;

$R^{14}$ is selected from the group consisting of H, halogen, $(C_1-C_6)$alkyl or $(C_1-C_6)$alkoxy;

$R^{15}$ is selected from the group consisting of H and $(C_1-C_6)$alkyl;

$R^{16}$ is selected from the group consisting of H, $(C_1-C_6)$alkyl-C(O)— and $(C_1-C_6)$alkyl-$SO_2$—;

$R^{17}$ is selected from the group consisting of $(C_1-C_6)$alkyl, $(C_1-C_6)$hydroxyalkyl, $(C_3-C_6)$cycloalkyl, $(C_1-C_6)$alkoxy$(C_1-C_6)$alkoxy, $(C_1-C_6)$alkoxy, $(C_1-C_6)$alkoxy$(C_1-C_6)$alkyl, allyl, propargyl, $R^8$-heteroaryl-, $R^8$-aryl- and $R^8$-aryl$(C_1-C_6)$alkyl-;

$R^{18}$ is selected from the group consisting of a bond, —$CH_2$—, —CH(OH)—, —$CH(CH_3)$—, —$C(CH_3)_n$—, —$(CH_2)_n$—, and —$O(CH_2)_n$—, $R^{19}$ is selected from the group consisting of H, $(C_1-C_6)$alkyl, $(C_1-C_6)$alkyl$(C_1-C_6)$cycloalkyl, $(C_1-C_6)$cycloalkyl$(C_1-C_6)$alkyl and $(C_1-C_6)$alkoxy$(C_1-C_6)$alkyl;

Q and $Q^1$ can be the same or different and are each independently selected from the group consisting of

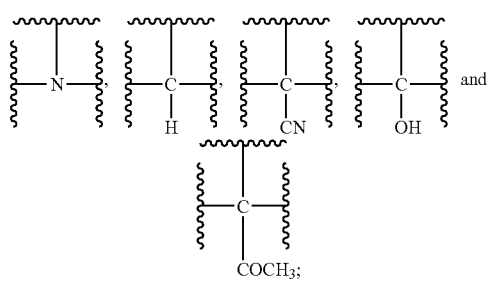

m and n are each independently 1-3;

p and q are each independently 0-2;

s is 0-4;

W is aryl or heteroaryl having 1-3 heteroatoms, which can be the same or different, and are independently selected from the group consisting of N, O and S, and wherein said aryl or heteroaryl is optionally substituted with 1-3 substituents, which can be the same or different, and are independently selected from the group consisting of alkyl, aryl, alkylcycloalkyl, halo, hydroxy, hydroxyalkyl, alkoxy, alkylalkoxy, alkoxyalkoxy, —$NR^6R^7$, $(C_2-C_6)$alkene, and —CN, or X is selected from the group consisting of H, $NH_2$, —$N(R^6)(CH_2)_s$-aryl, —$N(R^6)(CH_2)_s$-heteroaryl, —$N(R^6)(CH_2)_{m+1}$—OH, and —$N(CH_3)_2$, or X is —$R^{18}$—Y—Z;

Y is selected from the group consisting of —$N(R^6)CH_2CH_2N(R^7)$—, —$N(R^6)(CH_2)_n$aryl, —$OCH_2CH_2N(R^6)$—, —O—, —S—, —$CH_2S$—, —$(CH_2)_{2-3}$—$N(R^6)$—, $R^8$-divalent heteroaryl,

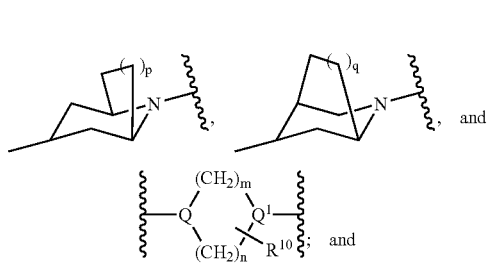

Z is selected from the group consisting of H, alkyl, alkoxyalkyl, $R^8$-aryl-, $R^8$-aryl($C_1$-$C_6$)alkyl-, $R^8$-heteroaryl-, $R^8$-bicyclicalkyl-, aminoalkyl, alkylamino, $NH_2$, —N—($R^6$)($CH_2$),-aryl, —N($R^6$)($CH_2$)$_s$-heteroaryl, —N($R_6$)C(O)O$R^{17}$, alkylcycloheteroalkyl, cycloheteroalkyl, cycloheteroalkylalkyl, alkoxycycloheteroalkyl, heteroaryl; $R^8$-benzofused heteroaryl-, diphenylmethyl and $R^9$—C(O)—; or when Y is

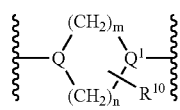

Z can also be —OH, $R^9$—$SO_2$—, $R^{17}$—N($R^{11}$)($CH_2$)$_s$—C(O)—, $R^{17}$—OC(O)—, $R^{17}$—O($CH_2$)$_n$C(O)—, benzofused heteroaryl($CH_2$)$_n$C(O)—, benzofused heteroaryl($CH_2$)$_n$— or $R^{17}$—N($R^{11}$)—C(S)—; or when Q is

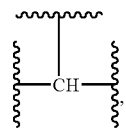

Z can also be $R^{17}R^{11}N$—, phenylamino or pyridylamino; or

Z and Y taken together are selected from the group consisting of

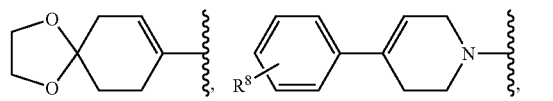

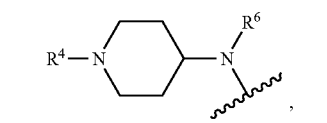

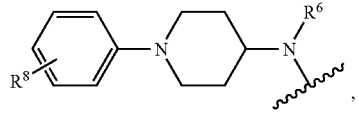

-continued

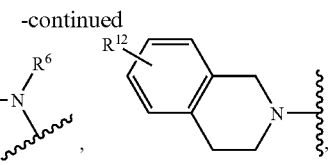

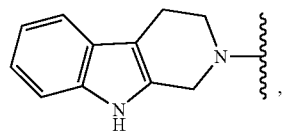

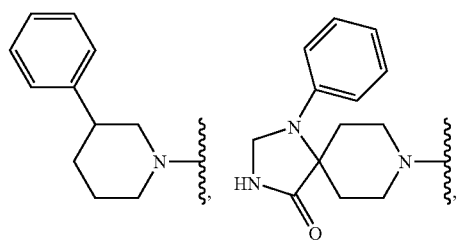

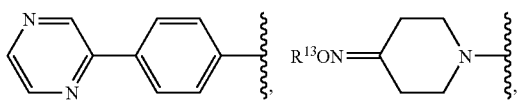

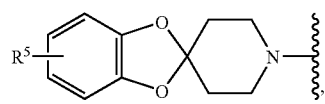

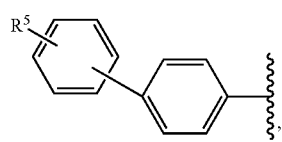

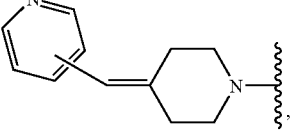

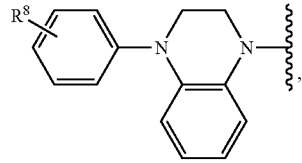

or an N-oxide thereof,

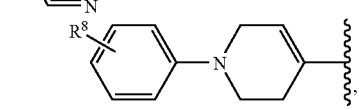

-continued
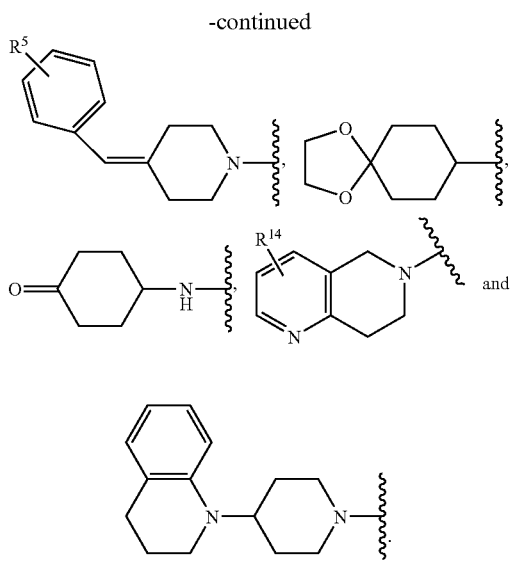
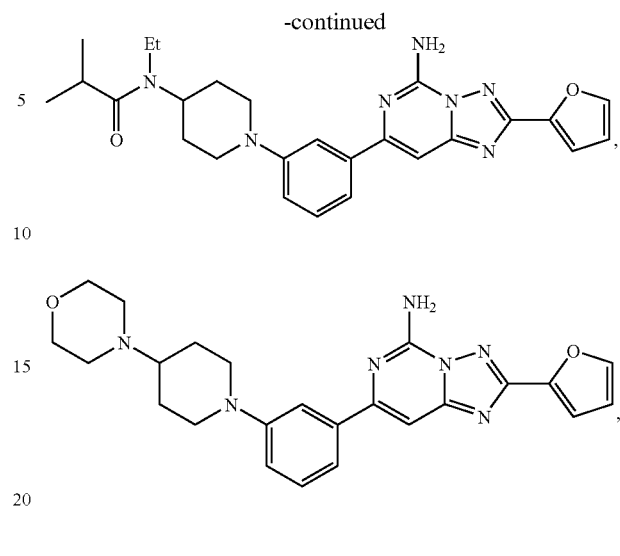
Preferred compounds of formula VII are those having the following structures:
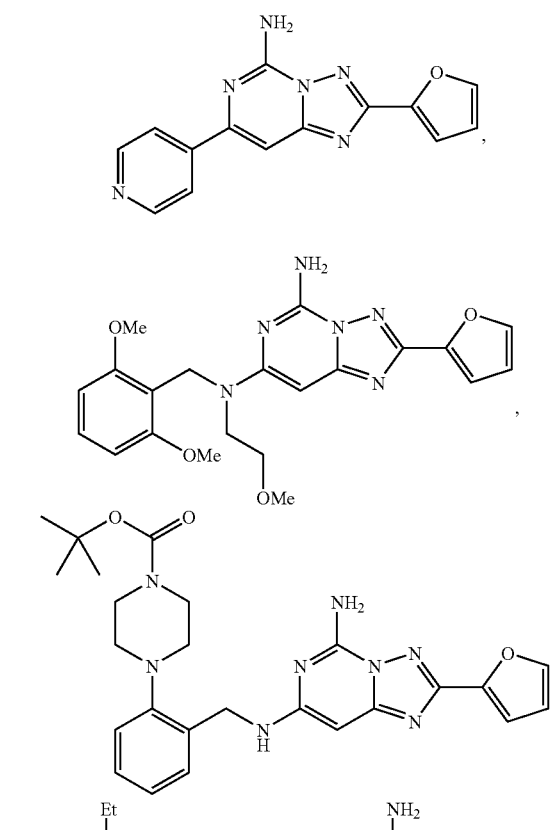
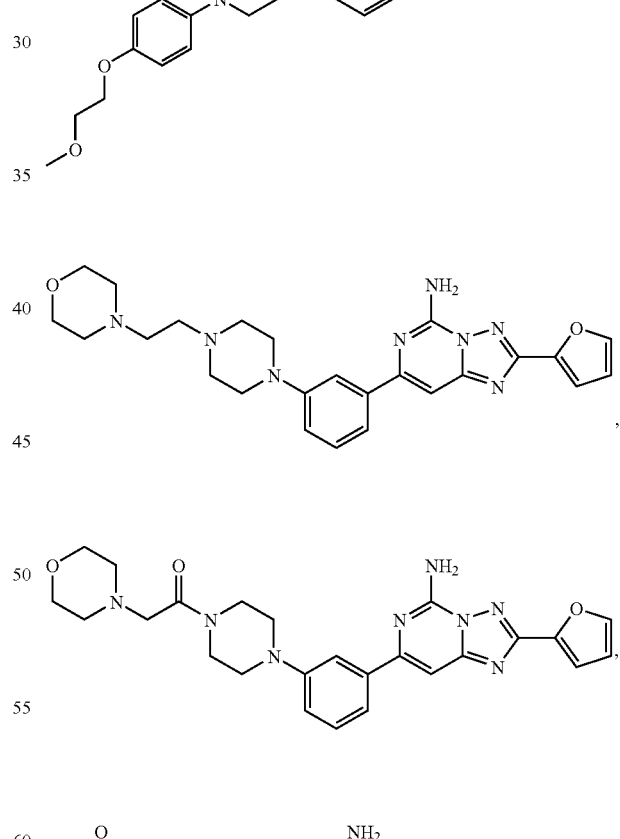
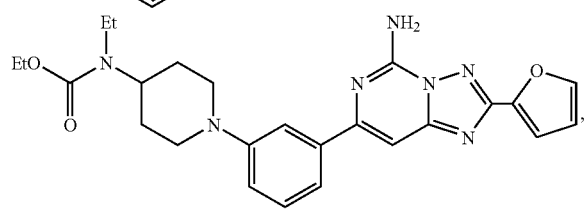

-continued

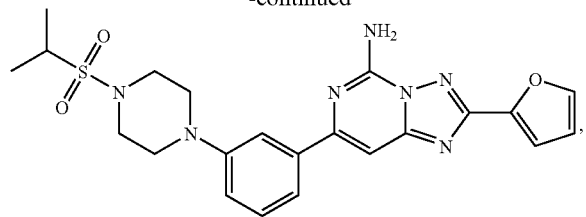

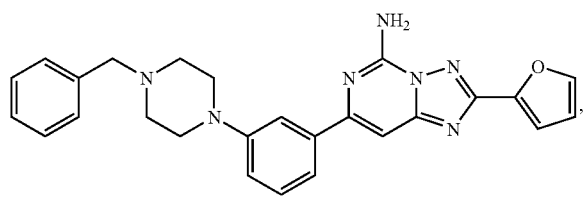

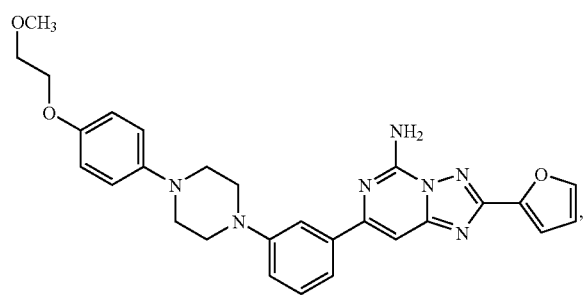

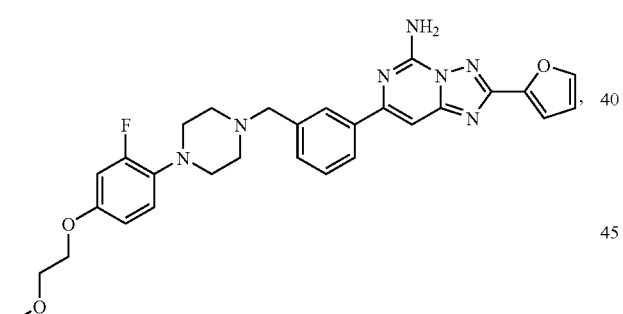

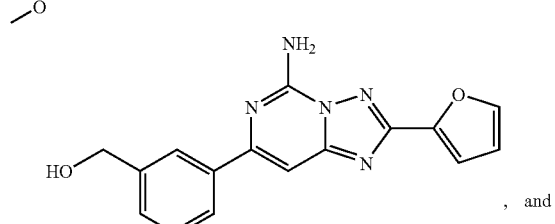

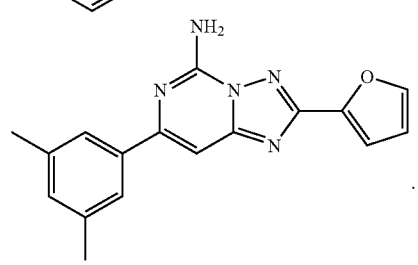

WO 03/048163 discloses useful adenosine $A_{2a}$ receptor antagonist compounds having the structural formula VIII

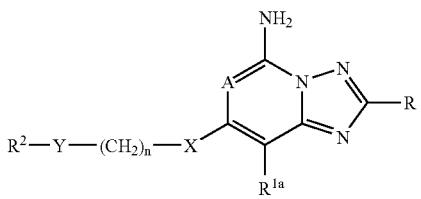

VIII or a pharmaceutically acceptable salt thereof, wherein:
A is $C(R^1)$ or N;
$R^1$ and $R^{1a}$ are independently selected from the group consisting of H, $(C_1-C_6)$-alkyl, halo, CN and $-CF_3$;
Y is $-O-$, $-S-$, $-SO-$, $-SO_2-$, $R^5$-heteroaryldiyl, $R^5$-arylene or

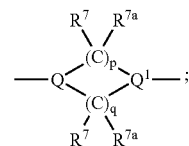

p and q are independently 2-3;
Q and $Q^1$ are independently selected from the group consisting of

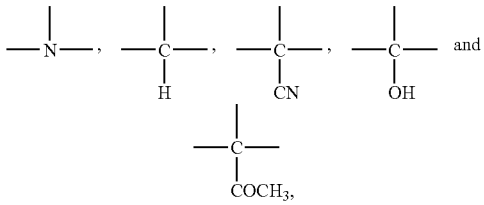

provided that at least one of Q and $Q^1$ is

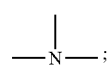

R is $R^5$-aryl, $R^5$-heteroaryl, $R^6-(C_2-C_6)$alkenyl or $R^6-(C_2-C_6)$alkynyl;
$R^2$ is $R^5$-aryl, $R^5$-heteroaryl, $R^5$-aryl$(C_1-C_6)$alkyl or $R^5$-heteroaryl$(C_1-C_6)$alkyl; or $R^2-Y$ is

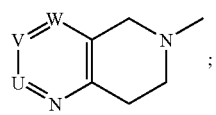

U, V, and W are independently selected from the group consisting of N and $CR^1$, provided that at least one of U, V and W is $CR^1$;

n is 1, 2 or 3; and
(a) A is C(R$^1$) and X is —C(R$^3$)(R$^{3a}$)—, —C(O)—, —O—, —S—, —SO—, —SO$_2$—, R$^4$-arylene, R$^4$-heteroaryldiyl, or —N(R$^9$)—; or A is C(R$^1$), Y is a bond, and X is —C(R$^3$)(R$^{3a}$)—, —C(O)—, —O—, —S—, —SO—, —SO$_2$—, R$^4$-arylene, —N(R$^9$)— or R$^4$-heteroaryldiyl, provided that when X is —N(R$^9$)— or R$^4$-heteroaryldiyl, R$^2$ is not phenyl or phenyl-(C$_1$-C$_6$)alkyl; or
(b) A is N, X is —N(R$^9$)—, Y is R$^5$-arylene and R$^2$ is

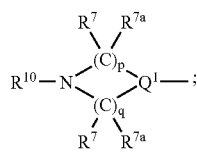

or n is 2 or 3; and
(c) A is N and X is —C(R$^3$)(R$^{3a}$)—, —C(O)—, —O—, —S—, —SO—, —SO$_2$—, —N(R$^9$)—, R$^4$-arylene or R$^4$-heteroaryldiyl; or A is N, Y is a bond and X is —C(O)—, —N(R$^9$)—, R$^4$-arylene or R$^4$-heteroaryldiyl; or A is N, Y is —N(R$^{9a}$)—, —C(O)N(R$^{9a}$)— or —O—(CH$_2$)$_2$—N(R$^{9a}$)—, and X is —N(R$^9$)—; or A is N, X is —N(R$^9$)—, and Y and R$^2$ together are

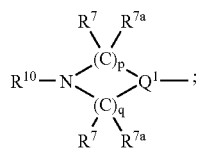

or n is 0; and
(d) A is N, Y is a bond, X is —N(R$^9$)—, and R$^2$ is

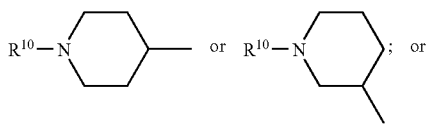

(e) A is N, X is —N(R$^9$)— and Y and R$^2$ together are

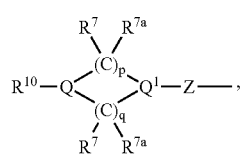

wherein Z is —C(O)—CH$_2$—, —C(O)—CH(C$_1$-C$_6$ alkyl)—, —CH$_2$—CH(C$_1$-C$_6$ alkyl)-, or —CH(C$_1$-C$_6$ alkyl)-CH$_2$—;

R$^3$ and R$^{3a}$ are independently selected from the group consisting of H, —OH, C$_1$-C$_6$ alkyl, hydroxy(C$_1$-C$_6$)alkyl, (C$_1$-C$_6$)alkoxy(C$_1$-C$_6$)alkyl, amino(C$_1$-C$_6$)alkyl, (C$_1$-C$_6$)alkylamino(C$_1$-C$_6$)alkyl and di(C$_1$-C$_6$)alkylamino(C$_1$-C$_6$)alkyl;

R$^4$ is 1-3 substituents selected from the group consisting of H, (C$_1$-C$_6$)alkyl, —OH, (C$_1$-C$_6$)alkoxy, (C$_1$-C$_6$)alkoxy(C$_1$-C$_6$)alkoxy, halo, —CF$_3$, and —CN;

R$^5$ is 1-3 substituents independently selected from the group consisting of H, (C$_1$-C$_6$)alkyl, —OH, (C$_1$-C$_6$)alkoxy, (C$_1$-C$_6$)alkoxy(C$_1$-C$_6$)alkyl, (C$_1$-C$_6$)alkoxy(C$_1$-C$_6$)-alkoxy, halo, —CF$_3$, —CN, —NH$_2$, (C$_1$-C$_6$)alkylamino, di(C$_1$-C$_6$)alkylamino, amino(C$_1$-C$_6$)-alkyl, (C$_1$-C$_6$)alkylamino(C$_1$-C$_6$)alkyl, di(C$_1$-C$_6$)alkylamino(C$_1$-C$_6$)alkyl, (C$_1$-C$_6$)alkanoylamino, (C$_1$-C$_6$)alkanesulfonylamino, (C$_1$-C$_6$)alkylthio, (C$_1$-C$_6$)alkylthio(C$_1$-C$_6$)alkyl, R$^6$—(C$_2$-C$_6$)alkenyl, R$^6$-(C$_2$-C$_6$)alkynyl, hydroxy(C$_1$-C$_6$)alkyl, (C$_1$-C$_6$)alkoxy-C(O)-amino, or heterocycloalkyl(C$_1$-C$_6$)alkyl;

R$^6$ is 1 to 3 substituents independently selected from the group consisting of H, —OH, (C$_1$-C$_6$)alkoxy and halo;

R$^7$ and R$^{7a}$ are independently selected from the group consisting of H, (C$_1$-C$_6$)alkyl, (C$_1$-C$_6$)alkoxy(C$_1$-C$_6$)alkyl, R$^8$-aryl and R$^8$-heteroaryl, or an R$^7$ and an R$^{7a}$ substituent on the same carbon can form =O;

R$^8$ is 1 to 3 substituents independently selected from H, (C$_1$-C$_6$)alkyl, —OH, (C$_1$-C$_6$)alkoxy, (C$_1$-C$_6$)alkoxy(C$_1$-C$_6$)alkoxy, halo, —CF$_3$, and —CN;

R$^9$ and R$^{9a}$ are independently selected from the group consisting of H, (C$_1$-C$_6$)alkyl, hydroxy(C$_2$-C$_6$)alkyl, (C$_1$-C$_6$)alkoxy(C$_2$-C$_6$)alkyl, amino(C$_2$-C$_6$)alkyl, (C$_1$-C$_6$)alkylamino(C$_2$-C$_6$)alkyl, di(C$_1$-C$_6$)alkylamino(C$_2$-C$_6$)alkyl, halo-(C$_3$-C$_6$)alkenyl, CF$_3$-(C$_1$-C$_6$)alkyl, (C$_3$-C$_6$)alkenyl, (C$_3$-C$_6$)cycloalkyl and (C$_3$-C$_6$)cycloalkyl-(C$_1$-C$_6$)alkyl; and R$^{10}$ is H, —C(O)—O—(C$_1$-C$_6$)alkyl, R$^5$-aryl, —C(O)—(C$_1$-C$_6$)alkyl, —C(O)—(R$^5$-aryl) or R$^5$-aryl-(C$_1$-C$_6$)alkyl.

Preferred compounds of formula VIII are those wherein A is N. R is preferably furyl. R$^{1a}$ is preferably hydrogen. Another group of preferred compounds is that wherein X is —O—, —S—, —N(R$^9$)— or R$^4$-arylene, with compounds wherein X is —N(R$^9$)— being more preferred. R$^9$ is preferably C$_1$-C$_6$ alkyl. Preferred definitions for Y are a bond or piperazinyl. R$^2$ is preferably R$^5$-aryl. When Y and/or R$^2$ is

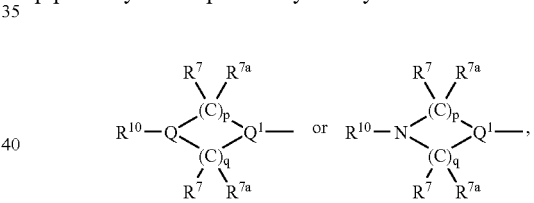

Q is preferably N, Q$^1$ is preferably N, p and q are each preferably 2, each R$^7$ and R$^{7a}$ is preferably hydrogen, and R$^{10}$ is preferably —C(O)—O—(C$_1$-C$_6$)alkyl, —C(O)—(C$_1$-C$_6$)alkyl or —C(O)—(R$^5$-aryl). R$^5$ is preferably 1 or 2 substituents selected from the group consisting of H, (C$_1$-C$_6$)alkoxy, (C$_1$-C$_6$)alkoxy(C$_1$-C$_6$)-alkoxy, halo and —CF$_3$. R$^4$ is preferably H, halo or (C$_1$-C$_6$)alkyl. R$^3$ and R$^{3a}$ are preferably independently selected from H and (C$_1$-C$_6$)alkyl. R$^{9a}$ is preferably H or (C$_1$-C$_6$)alkyl. R$^6$ is preferably hydrogen.

Preferred specific examples of compounds of formula VIII include compounds of the formula

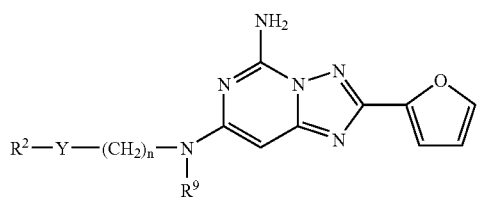

wherein R$^2$—Y—(CH$_2$)$_n$—N(R$^9$)— is as defined in the table:

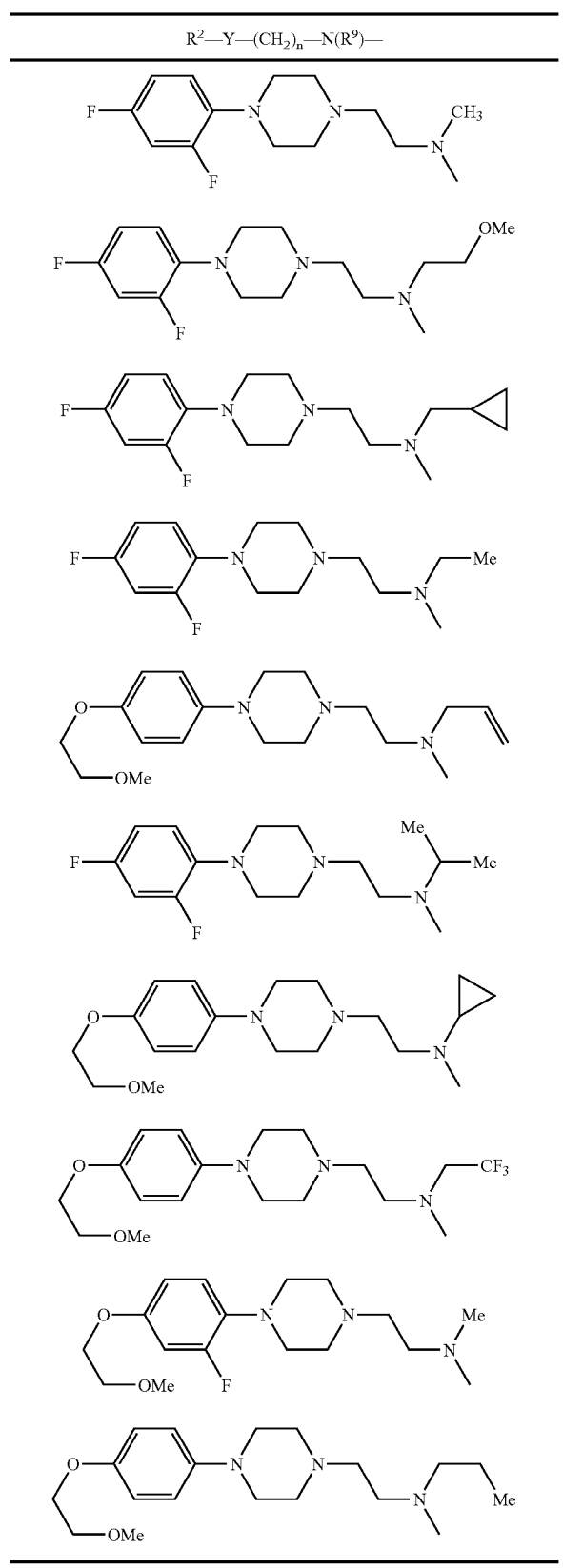

WO 01/02409 discloses useful adenosine $A_{2a}$ receptor antagonist compounds having the structural formula IX

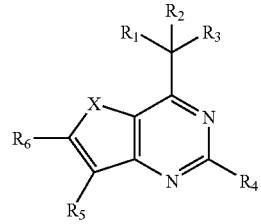

wherein

X is O or S;

$R_1$ and $R_2$ are independently selected from hydrogen, alkyl, aryl, hydroxy, alkoky, aryloxy, cyano, nitro, $CO_2R_7$, $COR_7$, $OCOR_7$, $CONR_7R_8$, $CONR_7NR_8R_9$, $OCONR_7R_8$, $NR_7R_8$, $NR_7COR_8$, $NR_7CONR_8R_9$, $NR_7CO_2R_8$, $NR_7SO_2R_8$, $NR_7CONR_8NR_9R_{10}$, $NR_7NR_8CO_2R_9$, $NR_7NR_8CONR_9R_{10}$, $NR_7SO_2NR_8R_9$, $SO_2R_7$, $SOR_7$, $SR_7$ and $SO_2NR_7R_8$, or $R_1$ and $R_2$ together form a carbonyl group (C=O), an oxime group (C=$NOR_{11}$), an imine group (C=$NR_{11}$) or a hydrazine group (C=$NNR_{11}R_{12}$), or $R_1$ and $R_2$ together form a 5, 6 or 7 membered carbocyclic or heterocyclic ring;

$R_3$ is alkyl or aryl;

$R_4$, $R_5$ and $R_6$ ate independently selected from hydrogen, alkyl, aryl, halogen, hydroxy, nitro, cyano, alkoxy, aryloxy, $CO_2R_7$, $COR_7$, $OCOR_7$, $SO_2R_7$, $SOR_7$, $SR_7$, $SO_2NR_7R_8$, $CONR_7R_8$, $CONR_7NR_8R_9$, $OCONR_7R_8$, $NR_7R_8$, $NR_7COR_8$, $NR_7CONR_8R_9$, $NR_7CO_2R_8$, $NR_7SO_2R_8$, $CR_7$=$NOR_8$, $NR_7CONR_8NR_9R_{10}$, $NR_7NR_8CO_2R_9$, $NR_7NR_8CONR_9R_{10}$, $SO_2NR_7NR_8R_9$, $NR_7SO_2NR_8R_9$, $NR_7NR_8SO_2R_9$, $NR_7NR_8CO_2R_9$, $NR_7NR_8R_9$ and $NR_7CSNR_8R_9$, or $R_5$ and $R_6$ together form a 5, 6 or 7 membered carbocyclic or heterocyclic ring; and $R_7$, $R_8$, $R_9$, $R_{10}$, $R_{11}$ and $R_{12}$ are independently selected from hydrogen, alkyl and aryl, or a pharmaceutically acceptable salt or prodrug thereof.

The US patents and applications cited herein are incorporated herein by reference. The adenosine $A_{2a}$ receptor antagonists are prepared by known methods as described in the cited patents and applications.

As used herein, "patient" means a mammal, especially a human.

It is contemplated that more than one adenosine $A_{2a}$ receptor antagonist (e.g., 2 or 3) can be administered to treat EPS, dystonia, RLS or PLMS; preferably, one adenosine $A_{2a}$ receptor antagonist is administered.

Antipsychotic agents causing the EPS treated by adenosine $A_{2a}$ receptor antagonists and for use in combination with adenosine $A_{2a}$ receptor antagonists include typical and atypical antipsychotic agents. Typical antipsychotics include loxapine, haloperidol, chlorpromazine, prochlorperazine and thiothixene. Atypical antipsychotics include clozapine, olanzapine, loxapine, quetiapine, ziprasidone and risperidone.

Tricyclic antidepressants causing dystonia treated by adenosine $A_{2a}$ receptor antagonists include perphenazine, amitriptyline, desipramine, doxepin, trimipramine and protriptyline. Anticonvulsants which may cause dystonia, but which also may be useful in treating ERLS or PLMS include phenytoin, carbamazepine and gabapentin.

Dopamine agonists useful in treating RLS and PLMS include pergolide, pramipexole, ropinerole, fenoldopam and cabergoline.

Opioids useful in treating PRLS and PLMS include codeine, hydrocodone, oxycodone, propoxyphene and tramadol.

Benzodiazepines useful in treating PRLS and PLMS include clonazepam, triazolam and temazepam.

The antipsychotics, tricyclic antidepressants, anticonvulsants, dopamine agonists, opioids and benzodiazepines are commercially available and are described in the literature, e.g., in The Physicians' Desk Reference (Montvale: Medical Economics Co., Inc., 2001).

It is contemplated that two or more $A_{2a}$ receptor antagonists could be administered in combination with one or more other agents (e.g., antipsychotics, tricyclic antidepressants, anticonvulsants, dopamine agonists, opioids or benzodiazepines), although administration of one $A_{2a}$ antagonist in combination with one other agent is preferred for each of the indications. While administration of separate dosage forms of the $A_{2a}$ antagonist(s) and the other agent(s) are preferred, it is also contemplated that the other agent(s) could be combined in a single dosage form with the $A_{2a}$ receptor antagonist(s) for the treatment or prevention of EPS, dystonia, RLS or PLMS.

Preferred adenosine A2a antagonists are those described in U.S. Pat. No. 6,630,475.

A particularly preferred compound of the invention is Compound A of the formula

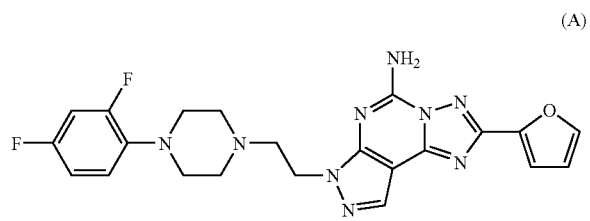

(A)

or a pharmaceutically acceptable salt or solvate thereof, disclosed in U.S. Pat. No. 6,630,475 and listed as the first compound in the table of compounds of structure I.

Compounds useful in the method of the invention will show utility as adenosine $A_{2a}$ receptor antagonists in these assays.

Human Adenosine $A_{2a}$ and $A_1$ Receptor Competition Binding Assay Protocol

Membrane sources: $A_{2a}$: Human $A_{2a}$ Adenosine Receptor membranes, Catalog #RB-HA2a, Receptor Biology, Inc., Beltsville, Md. Dilute to 17 µg/100 µl in membrane dilution buffer (see below).

Assay Buffers: Membrane dilution buffer: Dulbecco's Phosphate Buffered Saline (Gibco/BRL)+10 mM $MgCl_2$.

Compound Dilution Buffer: Dulbecco's Phosphate Buffered Saline (Gibco/BRL)+10 mM $MgCl_2$ supplemented with 1.6 mg/ml methyl cellulose and 16% DMSO. Prepared fresh daily.

Ligands: $A_{2a}$: [3H]-SCH 58261, custom synthesis, AmershamPharmacia Biotech, Piscataway, N.J. Stock is prepared at 1 nM in membrane dilution buffer. Final assay concentration is 0.5 nM.

$A_1$: [3H]-DPCPX, AmershamPharmacia Biotech, Piscataway, N.J. Stock is prepared at 2 nM in membrane dilution buffer. Final assay concentration is 1 nM.

Non-Specific Binding:

$A_{2a}$: To determine non-specific binding, add 100 nM CGS 15923 (RBI, Natick, Mass.). Working stock is prepared at 400 µM in compound dilution buffer.

$A_1$: To determine non-specific binding, add 100 µM NECA (RBI, Natick, Mass.). Working stock is prepared at 400 µM in compound dilution buffer.

Compound Dilution:

Prepare 1 mM stock solutions of compounds in 100% DMSO. Dilute in compound dilution buffer. Test at 10 concentrations ranging from 3 µM to 30 pM. Prepare working solutions at 4× final concentration in compound dilution buffer.

Assay Procedure:

Perform assays in deep well 96 well plates. Total assay volume is 200 µl. Add 50 µl compound dilution buffer (total ligand binding) or 50 µl CGS 15923 working solution ($A_{2a}$ non-specific binding) or 50 µl NECA working solution ($A_1$ non-specific binding) or 50 µl of drug working solution. Add 50 µl ligand stock ([3H]-SCH 58261 for $A_{2a}$, [3H]-DPCPX for $A_1$). Add 100 µl of diluted membranes containing the appropriate receptor. Mix. Incubate at room temperature for 90 minutes. Harvest using a Brandel cell harvester onto Packard GF/B filter plates. Add 45 µl Microscint 20 (Packard), and count using the Packard TopCount Microscintillation Counter. Determine $IC_{50}$ values by fitting the displacement curves using an iterative curve fitting program (Excel). Determine Ki values using the Cheng-Prusoff equation.

Haloieridol-Induced Catalepsy in the Rat

Male Sprague-Dawley rats (Charles River, Calco, Italy) weighing 175-200 g are used. The cataleptic state is induced by the subcutaneous administration of the dopamine receptor antagonist haloperidol (1 mg/kg, sc), 90 min before testing the animals on the vertical grid test. For this test, the rats are placed on the wire mesh cover of a 25×43 plexiglas cage placed at an angle of about 70 degrees with the bench table. The rat is placed on the grid with all four legs abducted and extended ("frog posture"). The use of such an unnatural posture is essential for the specificity of this test for catalepsy. The time span from placement of the paws until the first complete removal of one paw (descent latency) is measured maximally for 120 sec.

The selective $A_{2A}$ adenosine antagonists under evaluation are administered orally at doses ranging between 0.03 and 3 mg/kg, 1 and 4 h before scoring the animals.

In separate experiments, the anti-cataleptic effects were determined for the reference compound, L-DOPA (25, 50 and 100 mg/kg, ip), For preparing pharmaceutical compositions from the compounds useful in the method of this invention, inert, pharmaceutically acceptable carriers can be either solid or liquid. Solid form preparations include powders, tablets, dispersible granules, capsules, cachets and suppositories. The powders and tablets may be comprised of from about 0.1 to about 99 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds useful in the method of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the adenosine $A_{2a}$ receptor antagonist and the antipsychotic are administered orally.

Preferably, the pharmaceutical preparation is in unit dosage form. In such form, the preparation is subdivided into unit doses containing appropriate quantities of the active component, e.g., an effective amount to achieve the desired purpose.

The quantity of adenosine $A_{2a}$ receptor antagonist in a unit dose of preparation may be varied or adjusted from about 0.1 mg to 1000 mg, more preferably from about 1 mg to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the adenosine $A_{2a}$ receptor antagonist useful in the method of the invention will be regulated according to the judgment of the attending clinician considering such factors as age, condition and size of the patient as well as severity of the symptoms being treated. A typical recommended dosage regimen for an adenosine $A_{2a}$ receptor antagonist is oral administration of about 10 mg to 2000 mg/day preferably 10 to 1000 mg/day, in two to four divided doses to provide relief from the effects of EPS, dystonia, RLS or PLMS. The compounds are non-toxic when administered within this dosage range.

The doses and dosage regimen of the other agents used in combination with the adenosine $A_{2a}$ receptor antagonists, i.e., the antipsychotics, tricycicic antidepressants, anticonvulsants, dopamine agonists, benzodiazepines, opioids, lithium or iron, will be determined by the attending clinician in view of the approved doses and dosage regimen in the package insert, taking into consideration the age, sex and condition of the patient and the severity of the disease. When administered in combination, the adenosine $A_{2a}$ receptor antagonist and the other agent can be administered simultaneously or sequentially. This is particularly useful when the components of the combination are preferably given on different dosing schedules, e.g., one component is administered daily and the other every six hours, or when the preferred pharmaceutical compositions are different, e.g. one is preferably a tablet and one is a capsule. It is therefore advantageous to provide the adenosine $A_{2a}$ receptor antagonist and the other agent in a kit comprising, in separate containers in a single package, pharmaceutical compositions for use in combination to treat or prevent EPS, dystonia, RLS or PLMS, wherein one container comprises a pharmaceutical composition comprising an effective amount of an adenosine $A_{2a}$ receptor antagonist in a pharmaceutically acceptable carrier, and wherein a separate container comprises a pharmaceutical composition comprising an effective amount of another agent appropriate to treat the indicated condition.

Those skilled in the art will recognize that a dosage form for one of the components of the combination can be modified to contain both an adenosine $A_{2a}$ receptor antagonist and another agent, e.g., an adenosine $A_{2a}$ receptor antagonist and an antipsychotic or an adenosine $A_{2a}$ receptor antagonist and a dopamine agonist.

The following example shows the use of adenosine A2a antagonists to attenuate the Extra-Pyramidal Syndrome (EPS) displayed in *cebus apella* monkeys sensitized to the dopamine $D_2$ receptor antagonist, haloperidol.

EXAMPLE

A colony of seven *Cebus apella* monkeys that were previously sensitized to the chronic effects of haloperidol, exhibit EPS when administered haloperidol acutely (0.3 mg/kg, p.o.). Compound A was administered orally (p.o.) at doses of 0.3-30 mg/kg, in conjunction with haloperidol. The studies were conducted using a within-subjects design such that each monkey received all 6 treatments (vehicle and 5 doses of Compound A) in a crossover, balanced design. In all the studies, the group of seven monkeys exhibited baseline levels of EPS when dosed with haloperidol.

Figure 1B:
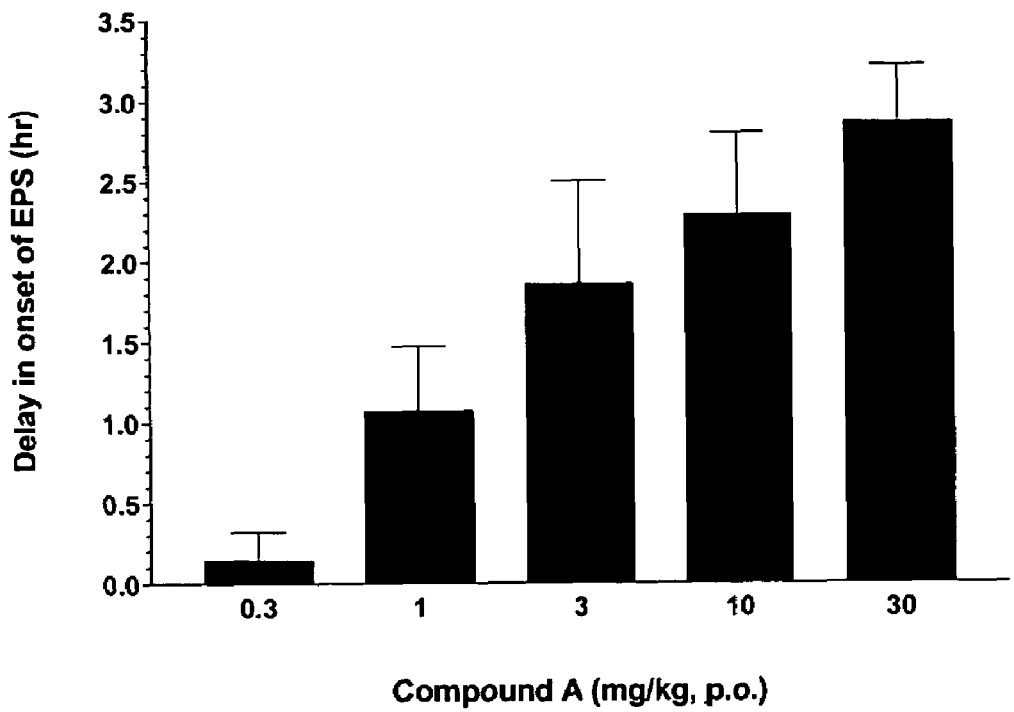
FIG. 1B represents the mean delay in onset of EPS for each treatment group compared to a vehicle control group.

Compound A produced a dose-dependent reduction in the maximum EPS score (FIG. 1A), as well as a dose-dependent delay in the onset of EPS (FIG. 1B). At a dose of 1 mg/kg, Compound A prevented the onset of EPS in one monkey, and delayed the onset of EPS by 1 hr. Compound A, at a dose of 3 mg/kg, prevented the onset of EPS in two monkeys, and delayed the onset of EPS by almost 2 hr in the remaining monkeys. At 10 and 30 mg/kg, Compound A prevented the onset of EPS in three monkeys and delayed the onset of EPS by an average of 2.3-2.9 hr.

Clinical guidelines for the treatment of RLS and PLMS have been established: see A. L. Chesson et al, *Sleep*, 22, 7 (1999), p. 961-8. Efficacy of adenosine $A_{2a}$ antagonists in treating RLS and PLMS can be determined by a method analogous to the clinical method described in the literature for pramipexole and ropinerole by Weimerskirch et al, *Annals of Pharmacotherapy*, 35, 5 (2001), p. 627-30.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A method for the treatment of Extra-Pyramidal Syndrome caused by treatment with an antipsychotic agent, comprising administering a therapeutically effective amount of an adenosine A2a receptor antagonist to a patient in need thereof, wherein the adenosine A2a antagonist is selected from the group consisting of compounds of the formula
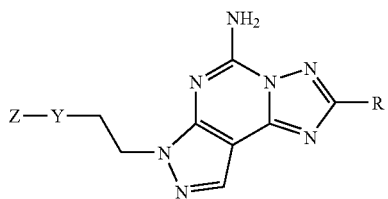
or a pharmaceutically acceptable salt or solvate thereof; wherein R and Z—Y are as defined in the following table:
| Z—Y— | R |
|---|---|
| 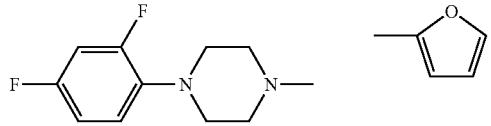 | 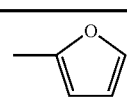 |
| 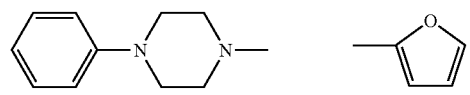 | 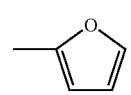 |
| 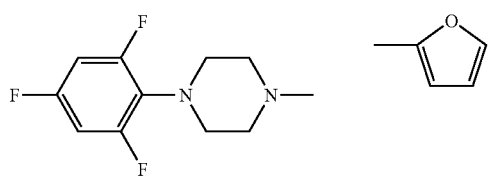 | 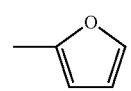 |
| 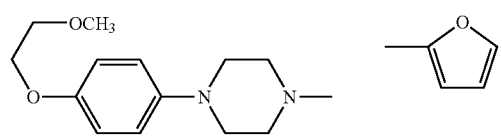 | 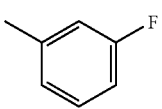 |
| 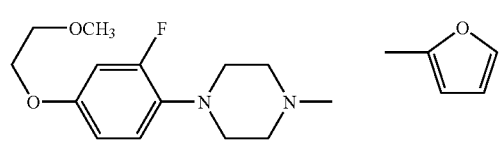 | 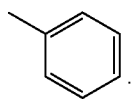 |
| 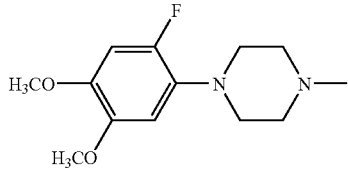 | 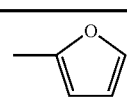 |
| 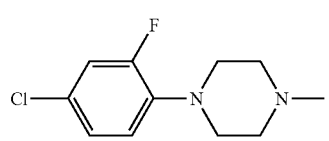 | 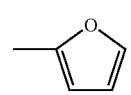 |
| 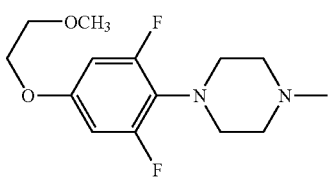 | 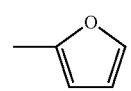 |
| 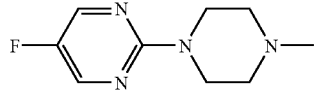 | 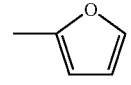 |
| 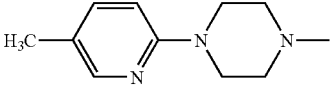 | 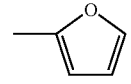 |
| 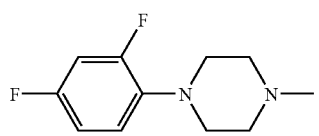 | 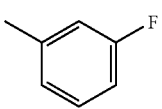 |
| 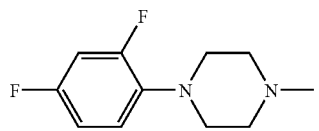 | 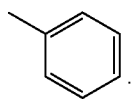 |
.

2. The method of claim 1 wherein the adenosine A2a antagonist is

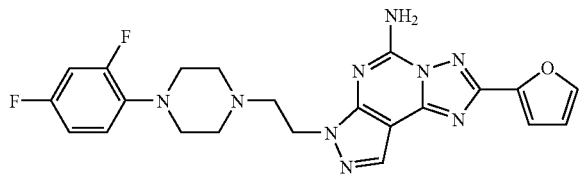

or a pharmaceutically acceptable salt or solvate thereof.

3. The method of claim 1 wherein the antipsychotic agent is a typical antipsychotic agent or and atypical antipsychotic agent.

4. The method of claim 3 wherein the typical antipsychotic agent is selected from the group consisting of loxapine, haloperidol, chlorpromazine, prochlorperazine and thiothixene, and the atypical antipsychotic agent is selected from the group consisting of clozapine, olanzapine, loxapine, quetiapine, ziprasidone and risperidone.

5. The method of claim 1 further comprising administering an antipsychotic agent in combination with the adenosine A2a receptor antagonist.

6. The method of claim 5 wherein the antipsychotic agent is a typical antipsychotic agent selected from the group consisting of loxapine, haloperidol, chlorpromazine, prochlorperazine and thiothixene, or an atypical antipsychotic agent selected from the group consisting of clozapine, olanzapine, loxapine, quetiapine, ziprasidone and risperidone.

7. A kit comprising, in separate containers in a single package, pharmaceutical compositions for use in combination to treat EPS caused by treatment with an antipsychotic agent, wherein one container comprises a pharmaceutical composition comprising an effective amount of an adenosine $A_{2a}$ receptor antagonist of claim 1 in a pharmaceutically acceptable carrier, and wherein, a separate container comprises a pharmaceutical composition comprising an effective amount of an antipsychotic agent.

8. A method for the treatment of Extra-Pyramidal Syndrome caused by treatment with an antipsychotic agent, comprising administering a therapeutically effective amount of an adenosine A2a receptor antagonist to a patient in need thereof, wherein the adenosine A2a antagonist is a compound of the formula

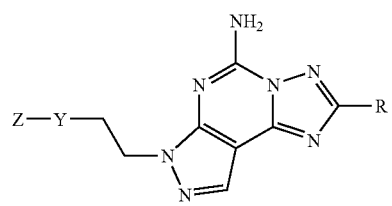

or a pharmaceutically acceptable salt or solvate thereof; wherein R and Z-Y are as defined below:

| Z—Y— | R |
|---|---|
| 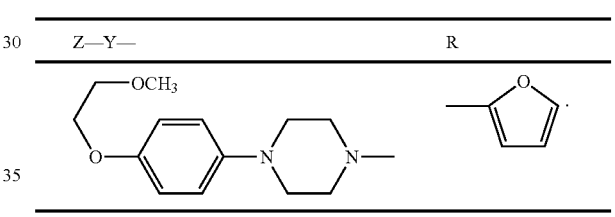 | |

* * * * *